(12) United States Patent
Domon et al.

(10) Patent No.: US 9,535,325 B2
(45) Date of Patent: Jan. 3, 2017

(54) ONIUM SALT, CHEMICALLY AMPLIFIED POSITIVE RESIST COMPOSITION, AND PATTERNING PROCESS

(71) Applicant: SHIN-ETSU CHEMICAL CO., LTD., Tokyo (JP)

(72) Inventors: Daisuke Domon, Jyoetsu (JP); Keiichi Masunaga, Jyoetsu (JP); Satoshi Watanabe, Jyoetsu (JP); Masahiro Fukushima, Jyoetsu (JP); Koji Hasegawa, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/573,871

(22) Filed: Dec. 17, 2014

(65) Prior Publication Data
US 2015/0198876 A1 Jul. 16, 2015

(30) Foreign Application Priority Data

Jan. 10, 2014 (JP) .................................. 2014-3243

(51) Int. Cl.
| | | |
|---|---|---|
| *G03F 7/004* | (2006.01) | |
| *C07C 61/125* | (2006.01) | |
| *C07C 61/29* | (2006.01) | |
| *G03F 7/039* | (2006.01) | |
| *G03F 7/32* | (2006.01) | |

(52) U.S. Cl.
CPC ........... *G03F 7/0392* (2013.01); *C07C 61/125* (2013.01); *C07C 61/29* (2013.01); *G03F 7/0045* (2013.01); *G03F 7/0046* (2013.01); *G03F 7/0397* (2013.01); *G03F 7/322* (2013.01)

(58) Field of Classification Search
CPC .... G03F 7/0045; G03F 7/0392; G03F 7/0046; G03F 7/0397; C07C 61/125; C07C 61/29
USPC ..... 430/270.1, 905, 910, 921, 922; 560/499, 560/502
See application file for complete search history.

(56) References Cited

U.S. PATENT DOCUMENTS

| | | |
|---|---|---|
| 2001/0036589 A1 | 11/2001 | Kinoshita et al. |
| 2001/0041300 A1 | 11/2001 | Kodama et al. |
| 2002/0051933 A1 | 5/2002 | Kodama et al. |
| 2004/0260031 A1 | 12/2004 | Takeda et al. |
| 2007/0043187 A1 | 2/2007 | Okamoto et al. |
| 2008/0096128 A1 | 4/2008 | Takeda et al. |
| 2008/0118860 A1 | 5/2008 | Harada et al. |
| 2009/0069521 A1 | 3/2009 | Nagai et al. |
| 2011/0160415 A1 | 6/2011 | Marchionni et al. |
| 2011/0294047 A1 | 12/2011 | Koitabashi et al. |
| 2012/0003583 A1 | 1/2012 | Tsuchimura et al. |
| 2012/0183893 A1 | 7/2012 | Watanabe et al. |
| 2012/0308920 A1 | 12/2012 | Domon et al. |

FOREIGN PATENT DOCUMENTS

| | | |
|---|---|---|
| EP | 1 338 921 A2 | 8/2003 |
| JP | H07-53456 A | 2/1995 |
| JP | A-11-327143 | 11/1999 |
| JP | 2001-281849 A | 10/2001 |
| JP | A-2004-115630 | 4/2004 |
| JP | A-2005-8766 | 1/2005 |
| JP | 2005-529116 A | 9/2005 |
| JP | 2007-504125 A | 3/2007 |
| JP | B2-3955384 | 8/2007 |
| JP | 2008-112186 A | 5/2008 |
| JP | A-2008-102383 | 5/2008 |
| JP | A-2008-111103 | 5/2008 |
| JP | B2-4116340 | 7/2008 |
| JP | A-2008-304590 | 12/2008 |
| JP | B2-4226803 | 2/2009 |
| JP | B2-4231622 | 3/2009 |
| JP | 2009-244805 A | 10/2009 |

(Continued)

OTHER PUBLICATIONS

Aug. 5, 2015 Office Action and Search Report issued in Taiwanese Patent Application No. 104100352.

(Continued)

*Primary Examiner* — John S Chu
(74) *Attorney, Agent, or Firm* — Oliff PLC

(57) ABSTRACT

The present invention provides the onium salt comprises the material represented by the following general formula (0-1),

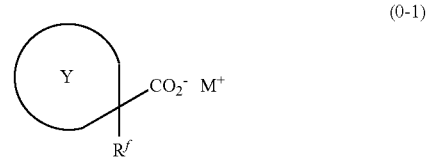

(0-1)

wherein $R^f$ represents a fluorine atom or a trifluoromethyl group; Y represents a cyclic hydrocarbon group having 3 to 30 carbon atoms, the hydrogen atom in the cyclic hydrocarbon group may be substituted by a hetero atom itself or a monovalent hydrocarbon group which may be substituted by a hetero atom(s), and the hetero atom(s) may be interposed into the cyclic structure of the cyclic hydrocarbon group and the monovalent hydrocarbon group; and $M^+$ represents a monovalent cation.

There can be provided an onium salt which can improve resolution at the time of forming a pattern and give a pattern with less line edge roughness (LER) when it is used in a chemically amplified positive resist composition.

7 Claims, No Drawings

(56) References Cited

FOREIGN PATENT DOCUMENTS

| | | |
|---|---|---|
| JP | 2010-039474 A | 2/2010 |
| JP | 2011-527362 A | 10/2011 |
| JP | B2-4801190 | 10/2011 |
| JP | 2012-013811 A | 1/2012 |
| TW | 201307273 A | 2/2013 |
| WO | 03/088967 A1 | 10/2003 |
| WO | WO 2006/121096 A1 | 11/2006 |

OTHER PUBLICATIONS

Aug. 9, 2016 Office Action issued in Japanese Application No. 2014-003243.

ONIUM SALT, CHEMICALLY AMPLIFIED POSITIVE RESIST COMPOSITION, AND PATTERNING PROCESS

BACKGROUND OF THE INVENTION

Field of the Invention

The present invention relates to an onium salt which can be used for preparing a chemically amplified positive resist composition to be used for processing of a semiconductor or a photomask blank, etc., a chemically amplified positive resist composition using the same and a resist patterning process using the composition.

Description of the Related Art

In recent years, as an integrated circuit progresses toward a higher integration, a finer circuit pattern profile has been required. Among these, a chemically amplified resist using an acid as a catalyst has been exclusively used in the patterning process of the size of 0.2 μm or less. Also, high-energy beam such as ultraviolet beam, far ultraviolet beam, electron beam, etc., has been used as a light source at this time, in particular, electron beam lithography which has been utilized as an ultrafine processing technology is indispensable as a processing method of a photomask blank used for producing a photomask for a semiconductor manufacturing.

A polymer containing a large amount of aromatic skeletons having an acidic side chain, for example, a polyhydroxystyrene, has been utilized as a resist composition for KrF excimer laser, but it shows remarkable absorption in wavelength of near 200 nm of the light, so that it has been never used as a resist composition for ArF excimer laser. However, it is an important material in the point that high etching resistance can be obtained as a resist composition for electron beam or a resist composition for extreme ultraviolet (EUV), which is a useful technology for forming a smaller pattern than the processing limit by ArF excimer laser.

In general, as a base polymer of a positive resist composition for electron beam or a resist composition for EUV, mainly used is a material in which an acid-labile protective group which protects the acidic functional group of the phenol side chain contained in the base polymer is deprotected by an acid generated from a photoacid generator by irradiating high-energy beam as a catalyst whereby it is solubilized in an alkaline developer. As the above-mentioned acid-labile protective group, a tertiary alkyl group, a t-butoxycarbonyl group, an acetal group, etc., have been mainly used. Here, when a protective group such as an acetal group which requires a relatively small activation energy necessary for deprotection is used, there is a merit that a high sensitivity resist film can be obtained, but if suppression of a generating acid diffusion is insufficient, the deprotection reaction occurs even in the unexposed area of the resist film, whereby there are problems that deterioration of line edge roughness (LER) or lowering in in-plane uniformity of a pattern line width (CDU) is generated.

Various improvements by selection or combination of a material(s) to be used for the resist composition, or change in the processing conditions, etc., have been investigated for controlling the above-mentioned resist sensitivity or pattern profile. As one of the points necessary for the improvement, there is a problem of diffusion of an acid which causes serious influence on resolution of a chemically amplified resist. The problem of the acid diffusion causes serious influence on sensitivity and resolution not only in the processing of a photomask but also in a general resist composition so that many investigations have been done.

An acid diffusion controlling agent is a material to suppress acid diffusion, and is in fact an essential component to improve performances of the resist, in particular resolution. Various investigations have been done on the acid diffusion controlling agent, and amines (Patent Document 1) or weak acid onium salts have generally been used. As an example of the weak acid onium salt, in Patent Document 2, it has been disclosed that good resist pattern can be formed without forming T-top, difference in line widths between isolated pattern and dense pattern, and standing wave by adding a triphenylsulfonium=acetate. Also, in Patent Document 3, it has been stated that sensitivity, resolution and exposure margin have been improved by the addition of a sulfonic acid ammonium salt or a carboxylic acid ammonium salt. Further, in Patent Document 4, it has been stated that a resist composition for KrF and electron beam comprising a combination containing a photoacid generator which generates a fluorine-containing carboxylic acid is excellent in resolution, and process admissibility such as exposure margin, depth of focus, etc., have been improved. Moreover, in Patent Document 5, it has been also stated that a resist composition for $F_2$ laser light comprising a combination containing a photoacid generator which generates a fluorine-containing carboxylic acid is excellent in line edge roughness (LER), and a problem of footing profile has been overcome. The above-mentioned documents concerning the onium salt relate to a material to be used for patterning using KrF, electron beam or $F_2$ lithography. In Patent Document 6, a positive photosensitive composition for ArF excimer laser exposure containing a carboxylic acid onium salt has been disclosed. These are to suppress the acid decomposition reaction of the acid-labile group and make the acid diffusion distance small (to control) by exchanging a strong acid (sulfonic acid) generated from the other photoacid generator by exposure with weak acid onium salt to form a weak acid and a strong acid=onium salt so that a strong acid (sulfonic acid) having high acidity is exchanged to a weak acid (carboxylic acid), and thus, it apparently acts as an acid diffusion controlling agent.

However, when patterning is carried out by using the above-mentioned resist composition containing a carboxylic acid onium salt or a fluorocarboxylic acid onium salt, it involves the problem that LER is large, so that development of an acid diffusion controlling agent which can reduce LER has been desired.

PRIOR ART REFERENCES

Patent Documents

Patent Document 1: Japanese Patent No. 4801190
Patent Document 2: Japanese Patent No. 3955384
Patent Document 3: Japanese Patent Laid-Open Publication No. H11-327143
Patent Document 4: Japanese Patent No. 4231622
Patent Document 5: Japanese Patent No. 4116340
Patent Document 6: Japanese Patent No. 4226803

SUMMARY OF THE INVENTION

The present invention has been accomplished in view of the above-mentioned circumstances, and an object thereof is to provide an onium salt which can improve resolution at the time of forming a pattern when it is used for a chemically amplified positive resist composition, and can give a pattern with less line edge roughness (LER).

To solve the above-mentioned problems, the present invention is to provide an onium salt represented by the following general formula (0-1),

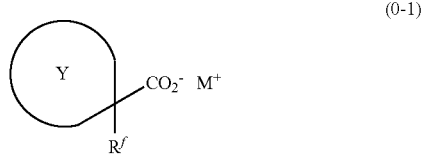

(0-1)

wherein $R^f$ represents a fluorine atom or a trifluoromethyl group; Y represents a cyclic hydrocarbon group having 3 to 30 carbon atoms, the hydrogen atom in the cyclic hydrocarbon group may be substituted by a hetero atom itself or a monovalent hydrocarbon group which may be substituted by a hetero atom(s), and the hetero atom(s) may be interposed into the cyclic structure of the cyclic hydrocarbon group and the monovalent hydrocarbon group; and $M^+$ represents a monovalent cation.

When such an onium salt is employed, acid diffusion by exposure at the time of forming a pattern can be effectively controlled when it is used in the chemically amplified positive resist composition, and as a result, a pattern improved in resolution and less LER can be obtained.

The above-mentioned onium salt is preferably a compound represented by the following general formula (1) or (2),

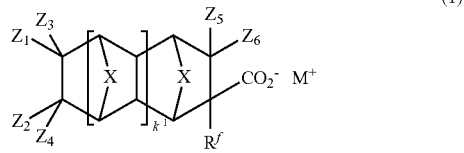

(1)

wherein $R^f$ and $M^+$ have the same meanings as defined above; X represents O or $CH_2$; $k^1$ represents an integer of 0 to 2; and $Z^1$, $Z^2$, $Z^3$, $Z^4$, $Z^5$ and $Z^6$ each independently represent a hydrogen atom or a linear, branched or cyclic monovalent hydrocarbon group having 1 to 10 carbon atoms which may be substituted by a hetero atom(s), and a hetero atom(s) may be interposed in the monovalent hydrocarbon group,

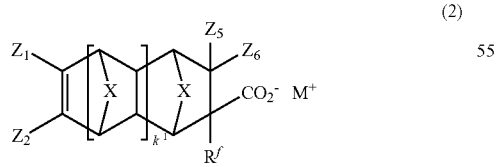

(2)

wherein $R^f$, X, $k^1$, $Z^1$, $Z^2$, $Z^5$, $Z^6$ and $M^+$ have the same meanings as defined above.

When such an onium salt is employed, resolution at the time of forming a pattern can be more improved when it is used in the chemically amplified positive resist composition, and handling thereof can be made easy.

The present invention is also to provide a chemically amplified positive resist composition comprising the above-mentioned onium salt, a resin having a group which can be decomposed by an acid, and a photoacid generator.

When such a chemically amplified positive resist composition is employed, acid diffusion can be effectively controlled by the action of the onium salt contained therein, so that when it is formed as a resist film and a pattern is formed, a pattern having good resolution and reduced in LER can be obtained.

Among these, the above-mentioned resin preferably contains a repeating unit represented by the following general formula (3),

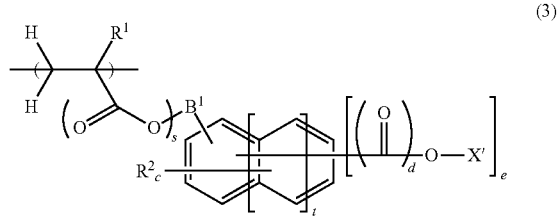

(3)

wherein "s" represents 0 or 1; "t" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "c" represents an integer satisfying $c \leq 5+2t-e$; "d" represents 0 or 1; "e" represents an integer of 1 to 3; and X' represents an acid-labile group when "e" represents 1, and represents a hydrogen atom or an acid-labile group when "e" represents 2 or more, and at least one of which represent an acid-labile group.

When such a chemically amplified positive resist composition is employed, the group protected by the acid-labile group in the above-mentioned repeating unit causes an deprotection reaction by the action of an acid, so that the composition shows good solubility in an alkaline developer.

Also, the above-mentioned resin preferably contains a repeating unit represented by the following general formula (4),

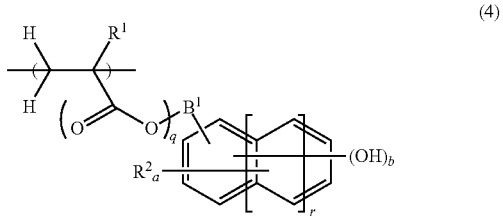

(4)

wherein "q" represents 0 or 1; "r" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "a" represents an integer satisfying $a \leq 5+2r-b$; and "b" represents an integer of 1 to 3.

When such a chemically amplified positive resist composition is employed, adhesion to the workpiece can be improved when it is formed as a resist film by the action of the above-mentioned repeating unit.

Further, the above-mentioned resin preferably contains a repeating unit represented by the following general formula (5) or a repeating unit represented by the following general formula (6), or both of them,

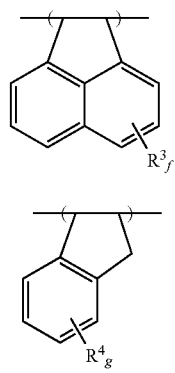

wherein "f" represents an integer of 0 to 6; each $R^3$ independently represents a hydrogen atom, an alkyl group having 1 to 6 carbon atoms which may be substituted by a halogen atom(s), a primary or secondary alkoxy group which may be substituted by a halogen atom(s) or an alkylcarbonyloxy group having 1 to 7 carbon atoms which may be substituted by a halogen atom(s); "g" represents an integer of 0 to 4; each $R^4$ independently represents a hydrogen atom, an alkyl group having 1 to 6 carbon atoms which may be substituted by a halogen atom(s), a primary or secondary alkoxy group which may be substituted by a halogen atom(s) or an alkylcarbonyloxy group having 1 to 7 carbon atoms which may be substituted by a halogen atom(s).

When such a chemically amplified positive resist composition is employed, etching selectivity to the workpiece at the time of forming a pattern can be improved by the action of the above-mentioned repeating unit.

Moreover, the above-mentioned chemically amplified positive resist composition preferably contains a basic compound.

When such a chemically amplified positive resist composition is employed, acid diffusion can be more effectively controlled, and a pattern having better resolution and more reduced in LER can be obtained.

Further, the present invention is to provide a patterning process which comprises the steps of forming a resist film on a workpiece using the above-mentioned chemically amplified positive resist composition, irradiating a high-energy beam to the resist film, and developing the resist film after irradiation using an alkaline developer to obtain a resist pattern.

When such a patterning process is employed, acid diffusion at the time of exposure can be effectively controlled by the action of the onium salt contained in the chemically amplified positive resist composition, so that a pattern with good resolution and reduced in LER can be formed onto the resist film.

At this time, EUV or an electron beam is preferably used as the above-mentioned high-energy beam.

When such a patterning process is employed, finer pattern can be formed onto the resist film.

In addition, a substrate having a layer containing chromium at the outermost layer is preferably used as the above-mentioned workpiece.

Further, a photomask blank is preferably used as the above-mentioned workpiece.

Thus, when the patterning process of the present invention is employed, even when a workpiece (for example, photomask blank) having an outermost layer which likely affects on a pattern profile of the chemically amplified resist such as a layer at the outermost containing chromium, etc., is used, a resist film excellent in adhesion can be obtained, and a pattern reduced in line edge roughness can be formed by exposure.

The chemically amplified positive resist composition containing the onium salt of the present invention can control acid diffusion effectively when the composition is exposed, and a pattern having extremely high resolution and reduced in LER can be obtained at the time of forming the pattern. Also, when such a patterning process using the chemically amplified positive resist composition is employed, a pattern having high resolution and reduced in LER can be formed, so that it can be suitably used for microprocessing technology, in particular, for electron beam and EUV lithography technology.

DETAILED DESCRIPTION OF THE PREFERRED EMBODIMENTS

In the following, the present invention is explained in more specifically.

The present inventors have studied to accomplish the above-mentioned problems, and as a result, they have found that a pattern with less LER can be obtained when an onium salt into which a fluorine atom or a trifluoromethyl group is introduced at an appropriate position of a carboxylic acid onium salt is added to a resist composition, whereby the present invention has been completed.

In the following, the present invention is explained in more detail.

Incidentally, in the following explanation, there exists an asymmetric carbon depending on the structure represented by the chemical formula, so that an enantio isomer (enantiomer) or a diastereo isomer (diastereomer) can exist in some cases, and in such a case, these isomers are represented by one formula as a representative. These isomers may be used alone, or may be used as a mixture.

The present invention is directed to an onium salt represented by the following general formula (0-1),

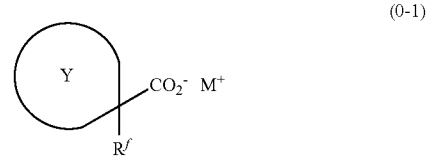

wherein $R^f$ represents a fluorine atom or a trifluoromethyl group; Y represents a cyclic hydrocarbon group having 3 to 30 carbon atoms, the hydrogen atom in the cyclic hydrocarbon group may be substituted by a hetero atom itself or a monovalent hydrocarbon group which may be substituted by a hetero atom(s), and the hetero atom(s) may be interposed into the cyclic structure of the cyclic hydrocarbon group and the monovalent hydrocarbon group; and M⁺ represents a monovalent cation.

A preferred embodiment of the onium salt represented by the above-mentioned general formula (0-1) is an onium salt represented by the following general formula (1) or (2),

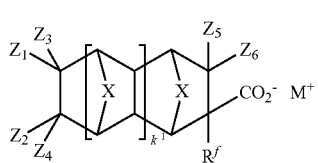

(1)

wherein $R^f$ and $M^+$ have the same meanings as defined above; X represents O or $CH_2$; $k^1$ represents an integer of 0 to 2; and $Z^1$, $Z^2$, $Z^3$, $Z^4$, $Z^5$ and $Z^6$ each independently represent a hydrogen atom or a linear, branched or cyclic monovalent hydrocarbon group having 1 to 10 carbon atoms which may be substituted by a hetero atom(s), and a hetero atom(s) may be interposed in the monovalent hydrocarbon group,

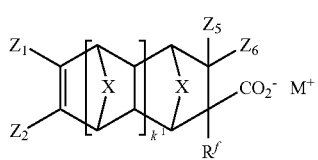

(2)

wherein $R^f$, X, $k^1$, $Z^1$, $Z^2$, $Z^5$, $Z^6$ and $M^+$ have the same meanings as defined above.

$M^+$ in the above-mentioned general formula (0-1), (1) and (2) represents a monovalent cation. The monovalent cation is not particularly limited, and may be mentioned a sulfonium cation represented by the following general formula (7),

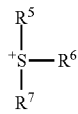

(7)

wherein each $R^5$, $R^6$ and $R^7$ independently represent a substituted or unsubstituted, linear or branched alkyl group, alkenyl group or oxoalkyl group each having 1 to 10 carbon atoms, or a substituted or unsubstituted aryl group, aralkyl group or aryloxoalkyl group each having 6 to 18 carbon atoms, and two or more of $R^5$, $R^6$ and $R^7$ may be bonded to each other to form a ring with the sulfur atom in the formula.

The above-mentioned alkyl group may be specifically mentioned a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, an adamantyl group, etc. The alkenyl group may be mentioned a vinyl group, an allyl group, a propenyl group, a butenyl group, a hexenyl group, a cyclohexenyl group, etc. The oxoalkyl group may be mentioned 2-oxocyclopentyl group, a 2-oxocyclohexyl group, a 2-oxo-propyl group, a 2-oxoethyl group, a 2-cyclopentyl-2-oxoethyl group, a 2-cyclohexyl-2-oxoethyl group, a 2-(4-methylcyclohexyl)-2-oxoethyl group, etc.

In addition, there may be mentioned the aryl group such as a phenyl group, a naphthyl group, a thienyl group, etc., the alkoxyphenyl group such as a 4-hydroxyphenyl group, a 4-methoxyphenyl group, a 3-methoxyphenyl group, a 2-methoxyphenyl group, a 4-ethoxyphenyl group, a 4-tert-butoxyphenyl group, a 3-tert-butoxyphenyl group, etc., the alkylphenyl group such as a 2-methylphenyl group, a 3-methylphenyl group, a 4-methylphenyl group, a 4-ethylphenyl group, a 4-tert-butylphenyl group, a 4-n-butylphenyl group, a 2,4-dimethylphenyl group, etc., the alkylnaphthyl group such as a methylnaphthyl group, an ethylnaphthyl group, etc., the alkoxynaphthyl group such as a methoxynaphthyl group, an ethoxynaphthyl group, etc., the dialkylnaphthyl group such as a dimethylnaphthyl group, a diethylnaphthyl group, etc., and the dialkoxynaphthyl group such as a dimethoxynaphthyl group, a diethoxynaphthyl group, etc. The aralkyl group may be mentioned a benzyl group, a 1-phenylethyl group, a 2-phenylethyl group, etc. The aryloxoalkyl group may be mentioned a 2-aryl-2-oxoethyl group such as a 2-phenyl-2-oxoethyl group, a 2-(1-naphthyl)-2-oxoethyl group, a 2-(2-naphthyl)-2-oxoethyl group, etc.

Also, when two or more of $R^5$, $R^6$ and $R^7$ are bonded to each other to form a ring with the sulfur atom in the formula, the group forming these cyclic structures may be mentioned a divalent organic group such as 1,4-butylene, 3-oxa-1,5-pentylene, etc. Further, there may be mentioned an aryl group having a polymerizable substituent(s) such as an acryloyloxy group, a methacryloyloxy group, etc., as a substituent(s), and specifically mentioned a 4-acryloyloxyphenyl group, a 4-methacryloyloxyphenyl group, a 4-acryloyloxy-3,5-dimethylphenyl group, a 4-methacryloyloxy-3,5-dimethylphenyl group, a 4-vinyloxyphenyl group, a 4-vinylphenyl group, etc.

The above-mentioned sulfonium cation may be specifically mentioned triphenyl sulfonium, 4-hydroxyphenyldiphenyl sulfonium, bis(4-hydroxyphenyl)phenyl sulfonium, tris(4-hydroxyphenyl)sulfonium, 4-tert-butoxyphenyldiphenyl sulfonium, bis(4-tert-butoxyphenyl)phenyl sulfonium, tris(4-tert-butoxyphenyl)sulfonium, 3-tert-butoxyphenyldiphenyl sulfonium, bis(3-tert-butoxyphenyl)phenyl sulfonium, tris(3-tert-butoxyphenyl)sulfonium, 3,4-di-tert-butoxyphenyldiphenyl sulfonium, bis(3,4-di-tert-butoxyphenyl)phenyl sulfonium, tris(3,4-di-tert-butoxyphenyl)sulfonium, diphenyl(4-thiophenoxyphenyl) sulfonium, 4-tert-butoxycarbonylmethyloxyphenyldiphenyl sulfonium, tris(4-tert-butoxycarbonylmethyloxyphenyl)sulfonium, (4-tert-butoxyphenyl)bis(4-dimethylaminophenyl) sulfonium, tris(4-dimethylaminophenyl) sulfonium, 2-naphthyldiphenyl sulfonium, (4-hydroxy-3,5-dimethylphenyl) diphenyl sulfonium, (4-n-hexyloxy-3,5-dimethylphenyl) diphenyl sulfonium, dimethyl(2-naphthyl)sulfonium, 4-hydroxyphenyldimethyl sulfonium, 4-methoxyphenyldimethyl sulfonium, trimethyl sulfonium, 2-oxocyclohexylcyclohexylmethyl sulfonium, trinaphthyl sulfonium, tribenzyl sulfonium, diphenylmethyl sulfonium, dimethylphenyl sulfonium, 5-phenyldibenzothiophenium, 10-phenylphenoxathiinium, 2-oxo-2-phenylethylthiacyclopentanium, diphenyl2-thienyl sulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, 4-methylphenyldiphenyl sulfonium, 4-ethylphenyldiphenyl sulfonium, 4-tert-butylphenyldiphenyl sulfonium, 4-cyclohexylphenyldiphenyl sulfonium, 4-n-hexylphenyldiphenyl sulfonium, 4-n-octylphenyldiphenyl sulfonium, 4-methoxyphenyldiphenyl sulfonium, 4-ethoxyphenyldiphenyl sulfonium, 4-tert-butoxyphenyldiphenyl sulfonium, 4-cyclohexyloxyphenyl-diphenyl sulfonium, 4-n-hexyloxyphenyldiphenyl sulfonium, 4-n-octyloxyphenyldiphenyl sulfonium, 4-dodecyloxyphenyldiphenyl sulfonium, 4-trifluoromethylphenyldiphenyl sulfonium, 4-trifluoromethyloxyphenyldiphenyl sulfonium, 4-tert-butoxycarbonylmethyloxyphenyldiphenyl sulfonium, 4-methacryloyloxyphenyldiphenyl sulfonium, 4-acryloyloxy-phenyldiphenyl sulfonium, (4-n-hexyloxy-3,5-dimethyl-phenyl)diphenyl sulfonium, (4-methacryloyloxy-3,5-dimethylphenyl)diphenyl sulfonium, (4-acryloyloxy-3,5-dimethylphenyl)diphenylsulfonium, etc.

It is more preferably mentioned triphenyl sulfonium, 4-tert-butylphenyldiphenyl sulfonium, 4-tert-butoxyphenyldiphenyl sulfonium, tris(4-tert-butylphenyl)sulfonium, 4-tert-butoxycarbonylmethyloxyphenyldiphenyl sulfonium, 4-methacryloyloxyphenyldiphenyl sulfonium, 4-acryloyloxy-phenyldiphenyl sulfonium, 4-methacryloyloxyphenyldimethyl sulfonium, 4-acryloyloxyphenyldimethyl sulfonium, (4-methacryloyloxy-3,5-dimethylphenyl)diphenyl sulfonium, (4-acryloyloxy-3,5-dimethylphenyl)diphenyl sulfonium, etc.

Also, the monovalent cation represented by $M^+$ in the above-mentioned general formulae (0-1), (1) and (2) may be mentioned, other than the sulfonium cation, an iodonium cation and an ammonium cation, etc.

More specific iodonium cation may be exemplified by diphenyliodonium, bis(4-methylphenyl)iodonium, bis(4-(1,1-dimethylethyl)phenyl)iodonium, bis(4-(1,1-dimethylpropyl)phenyl)iodonium, (4-(1,1-dimethylethoxy)phenyl)phenyliodonium, etc., and the ammonium cation may be exemplified by a tertiary ammonium salt such as a salt of trimethylammonium, triethylammonium, tributylammonium, N,N-dimethylanilinium, etc., or a quaternary ammonium salt such as a salt of tetramethylammonium, tetraethylammonium, tetrabutylammonium, etc.

In the above-mentioned general formulae (1) and (2), each $Z^1, Z^2, Z^3, Z^4, Z^5$ and $Z^6$ independently represent a hydrogen atom or a linear, branched or cyclic monovalent hydrocarbon group having 1 to 10 carbon atoms which may be substituted by a hetero atom(s), and a hetero atom(s) may be interposed in the monovalent hydrocarbon group. Such a monovalent hydrocarbon group may be specifically exemplified by a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0$^{2,6}$]decanyl group, an adamantyl group, etc. Also, a part of the hydrogen atom(s) of these groups may be substituted by a hetero atom(s) such as an oxygen atom, a sulfur atom, a nitrogen atom, a halogen atom, etc., or a hetero atom(s) such as an oxygen atom, a sulfur atom, a nitrogen atom, etc., may be interposed therebetween. That is, they may form or may be interposed by a hydroxyl group, a cyano group, a carbonyl group, an ether bond, an ester bond, a sulfonate ester bond, a carbonate bond, a lactone ring, a sultone ring, a carboxylic acid anhydride, a haloalkyl group, etc.

Preferred specific examples of the carboxylic acid anion in the above-mentioned general formulae (1) or (2) are shown below.

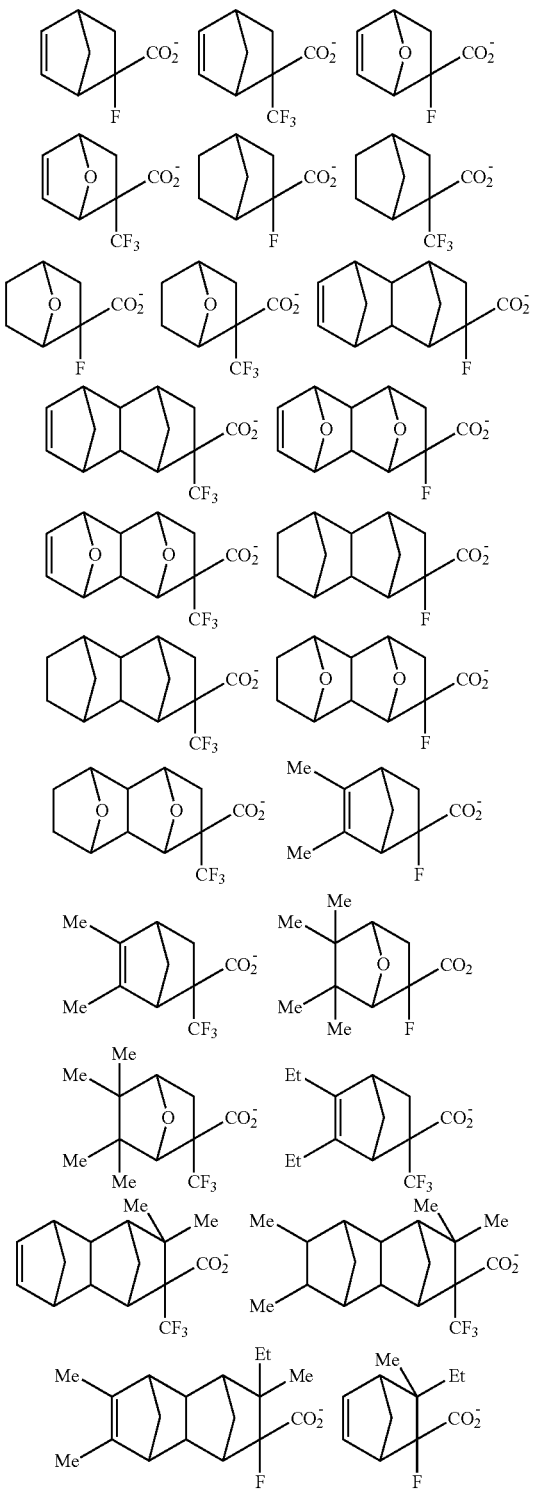

A method for obtaining the onium salt represented by the above-mentioned general formula (2) is exemplified by the following reaction scheme, but the invention is not limited by these.

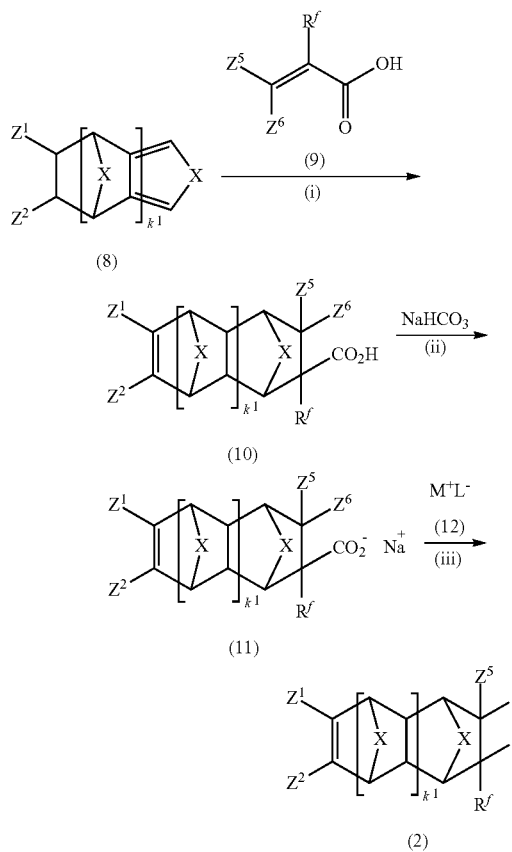

wherein $R^f$, $X$, $k^1$, $Z^1$, $Z^2$, $Z^5$, $Z^6$ and $M^+$ have the same meanings as defined above; and $L^-$ represents a halide ion or a methyl sulfate ion.

The step (i) in the above-mentioned scheme is a step to give a carboxylic acid (10) by the Diels-Alder reaction of a diene (8) and a fluorinated acrylic acid (9). The reaction may be preferably carried out without solvent or in a solvent such as methylene chloride, toluene, hexane, diethyl ether, tetrahydrofuran, acetonitrile, etc., by mixing the diene (8) and the fluorinated acrylic acid (9), under cooling or heating, if necessary.

The step (ii) is a step to convert the carboxylic acid (10) to a sodium salt (11). The solvent which can be used for the reaction may be mentioned water, ethers such as tetrahydrofuran, diethyl ether, diisopropyl ether, di-n-butyl ether, 1,4-dioxane, etc., hydrocarbons such as n-hexane, n-heptane, benzene, toluene, xylene, etc., aprotic polar solvents such as acetonitrile, dimethylsulfoxide (DMSO), N,N-dimethylformamide (DMF), etc., chlorinated organic solvents such as methylene chloride, chloroform, carbon tetrachloride, etc. These solvents may be used by optionally selecting depending on the reaction conditions, and may be used one kind alone or two or more kinds in admixture. The reaction may be preferably carried out in the above-mentioned solvent by mixing the carboxylic acid (10) and sodium hydrogen carbonate, under cooling or heating, if necessary.

The step (iii) is a step of obtaining an objective onium salt (2) by an ion-exchange reaction of the sodium salt of a carboxylic acid (11) and an onium salt (12). The solvent which can be used for the reaction may be mentioned water, ethers such as tetrahydrofuran, diethyl ether, diisopropyl ether, di-n-butyl ether, 1,4-dioxane, etc., hydrocarbons such as n-hexane, n-heptane, benzene, toluene, xylene, etc., aprotic polar solvents such as acetonitrile, dimethylsulfoxide (DMSO), N,N-dimethylformamide (DMF), etc., chlorinated organic solvents such as methylene chloride, chloroform, carbon tetrachloride, etc. These solvents may be used by optionally selecting depending on the reaction conditions, and may be used one kind alone or two or more kinds in admixture. The reaction may be preferably carried out in the above-mentioned solvent by mixing the carboxylic acid salt (11) and the onium salt (12), under cooling or heating, if necessary. The objective onium salt (2) can be obtained from the reaction mixture by the usual post-treatment of the aqueous system (aqueous work-up), and can be purified by the conventional method such as recrystallization, chromatography, etc., if necessary.

A method for obtaining the onium salt represented by the general formula (1') in which $Z^3$ and $Z^4$ in the above-mentioned general formula (1) are hydrogen atoms is exemplified by the following reaction scheme, but the invention is not limited by these,

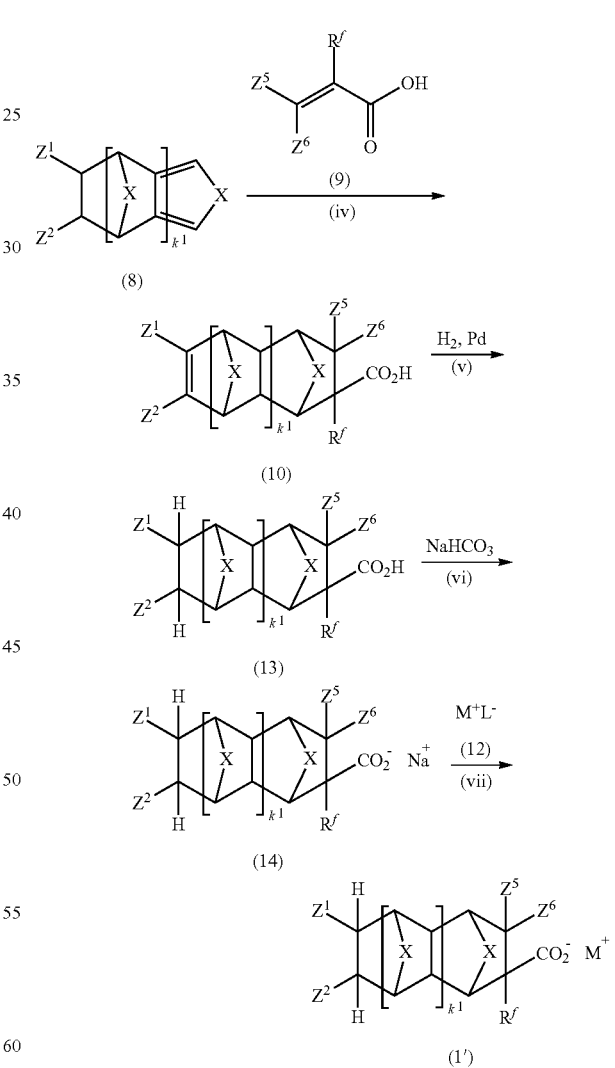

wherein $R^f$, $X$, $k^1$, $Z^1$, $Z^2$, $Z^5$, $Z^6$, $M^+$ and $L^-$ have the same meanings as defined above.

The above-mentioned step (iv) is the same as the step (i) in the scheme for obtaining the onium salt represented by the above-mentioned general formula (2).

The above-mentioned step (v) is a step to obtain a carboxylic acid (13) by hydrogenating the double bond of the carboxylic acid (10) by hydrogenation reaction. The reaction may be preferably carried out without solvent or in a solvent such as methylene chloride, methanol, toluene, hexane, diethyl ether, tetrahydrofuran, acetonitrile, etc., by mixing a palladium catalyst and the carboxylic acid (10), and stirring the same under hydrogen atmosphere. In addition, it may be carried out under cooling or heating, if necessary.

The above-mentioned steps (vi) and (vii) are the same as the step (iii) and the step (iv), respectively, in the scheme for obtaining the onium salt represented by the above-mentioned general formula (2). That is, the step (vi) is a step of converting the carboxylic acid (13) to a sodium salt (14), and the step (vii) is a step of obtaining an objective onium salt (1') by an ion-exchange reaction of the sodium salt (14) and an onium salt (12).

Among the above-mentioned schemes, the onium salt (12) to be used in the ion-exchange reaction with the carboxylic acid salts (11, 13) is not particularly limited, and may be exemplified by a sulfonium salt, an iodonium salt, an ammonium salt, etc., which can give the above-mentioned sulfonium cation, iodonium cation or ammonium cation.

When the onium salt represented by the above-mentioned general formula (0-1) of the present invention, in particular, the onium salt represented by the above-mentioned general formula (1) or (2) is formulated in the chemically amplified resist composition, a strong acid (sulfonic acid, etc.) generated from the other photoacid generator by exposure is exchanged with the onium salt of the present invention, to form a weak acid and a strong acid=onium salt whereby exchanging from a strong acid (sulfonic acid, etc.) having high acidity to a weak acid (carboxylic acid). It is to suppress the acid decomposition reaction of the acid-labile group as a result, and to make the acid diffusion distance small (to control), whereby it apparently acts as an acid diffusion controlling agent. The onium salt of the present invention contains a fluorine atom(s) at the α-position of the carboxyl group or a fluoroalkyl group so that acidity thereof is considered to be increased as compared with the carboxylic acid the α-position of which is not substituted. As a result, the difference of a pKa thereof from that of the strong acid such as sulfonic acid, etc., becomes small, so that a rapid exchange reaction is considered to be easily caused, and this is considered to be contributed to lower the roughness such as LER.

Acidity of the acid generated from the onium salt preferably has a pKa in the range of 1.5 to 4.0, more preferably in the range of 1.5 to 3.5. If the pKa is 1.5 or more, there is no fear of increasing the acidity than required, and it can function sufficiently as the acid diffusion controlling agent. On the other hand, if the pKa is 4.0 or less, the difference in the pKa thereof from that of the acid generated from the photoacid generator is not so large, and it does not completely trap the acid, so that the above-mentioned sufficient effect of reducing roughness by the exchange reaction of the acid and the onium salt can be obtained.

Also, the onium salt represented by the above-mentioned general formula (1) or (2) of the present invention contains a bulky alicyclic structure, so that it can be considered that migration and diffusion of the strong acid can be more effectively controlled. Incidentally, the onium salt represented by the above-mentioned general formula (1) or (2) of the present invention has sufficient lipophilicity so that producing and handling thereof are easy.

When it is such an onium salt, it can be suitably used as a material of the chemically amplified positive resist composition mentioned later.

[Chemically Amplified Positive Resist Composition]

The present invention is to provide a chemically amplified positive resist composition containing the onium salt represented by the above-mentioned general formulae (0-1), (1), or (2). As such a chemically amplified positive resist composition, there may be mentioned, for example, a chemically amplified resist composition comprising the above-mentioned onium salt, an acid generator and a base resin. For preparing the positive resist composition, it is preferred to contain, as a base resin, a resin having a group which can be decomposed by an acid, i.e., a resin which is decomposed by an action of an acid, and solubility thereof in an alkaline developer increases (hereinafter referred to as "base resin").

In the chemically amplified positive resist composition of the present invention, a unit having an acidic functional group protected by an acid-labile group (a unit protected by an acid-labile group, and deprotected by an action of an acid to become alkali soluble) is preferably contained in the base resin, for the purpose of providing the characteristics that the exposed area is dissolved in an aqueous alkali solution as the positive resist. The most preferred unit which is protected by an acid-labile group, and becomes alkali soluble by the action of an acid may be mentioned the repeating unit represented by the following general formula (3),

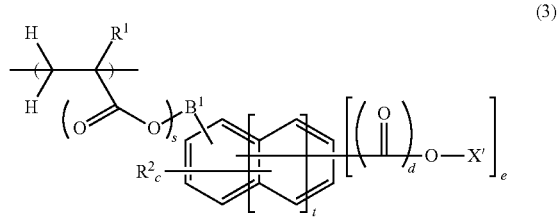

(3)

wherein "s" represents 0 or 1; "t" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "c" represents an integer satisfying c≤5+2t−e; "d" represents 0 or 1; "e" represents an integer of 1 to 3; and X' represents an acid-labile group when "e" represents 1, and represents a hydrogen atom or an acid-labile group when "e" represents 2 or more, and at least one of which represent an acid-labile group.

Also, the above-mentioned base resin desirably contain a repeating unit represented by the following general formula (4),

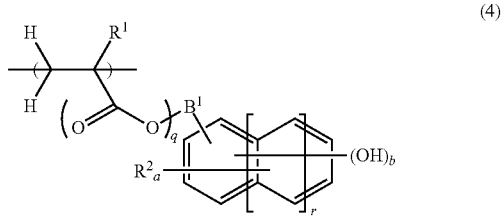

(4)

wherein "q" represents 0 or 1; "r" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "a" represents an integer satisfying a≤5+2r−b; and "b" represents an integer of 1 to 3.

Among the above-mentioned general formula (4), the repeating unit (i.e., q=0) without the linker (—CO—O—$B^1$—) is a unit derived from a monomer having a substituted or unsubstituted vinyl group at its 1-position that is bonded to an aromatic ring substituted with a hydroxyl group, which is represented by a hydroxystyrene unit, etc., and preferred specific examples thereof may be mentioned a unit derived from 3-hydroxystyrene, 4-hydroxystyrene, 5-hydroxy-2-vinylnaphthalene or 6-hydroxy-2-vinylnaphthalene, etc.

The repeating unit when it has a linker (—CO—O—$B^1$—) is a unit derived from a vinyl monomer substituted with a carbonyl group, which is represented by a (meth)acrylate ester. Specific examples of the repeating unit represented by the above-mentioned general formula (4) which has a linker (—CO—O—$B^1$—) are shown below.

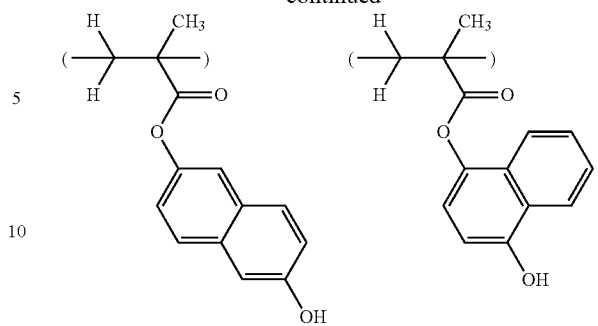

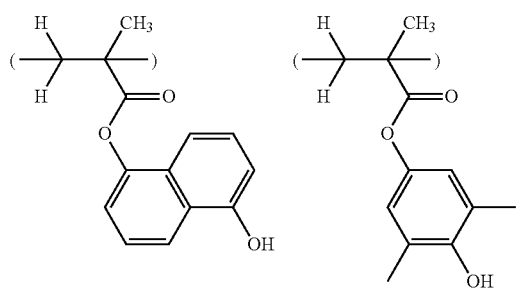

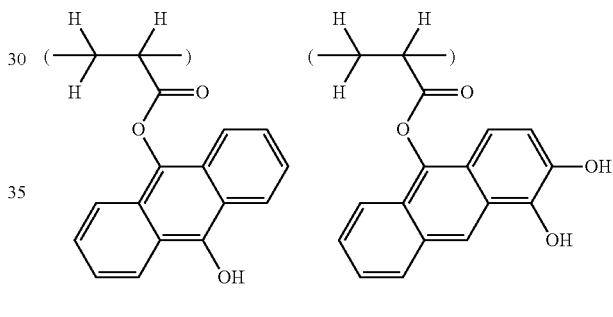

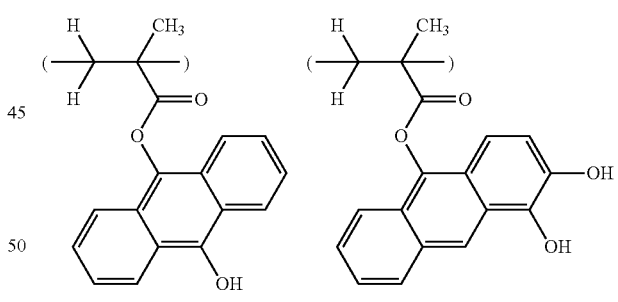

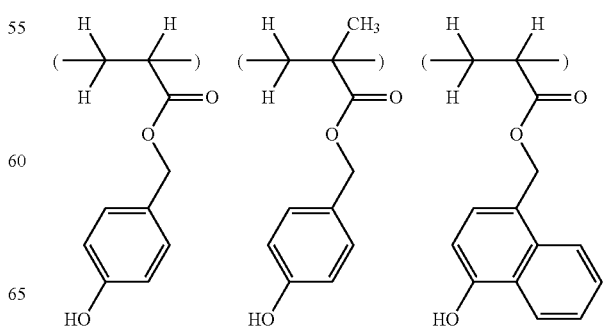

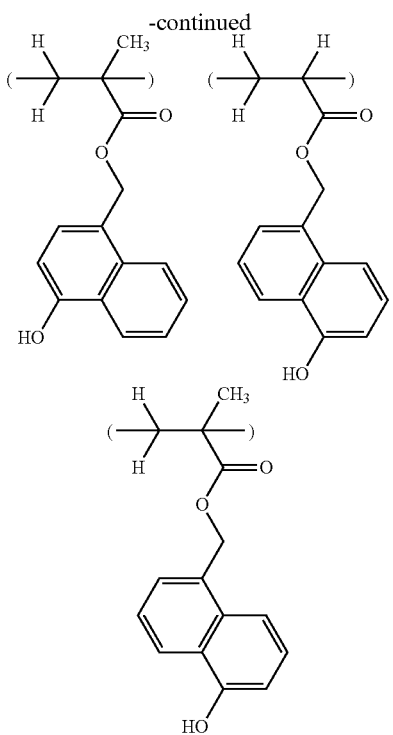

The unit represented by the above-mentioned general formula (4) may be used one kind alone, or may be used in combination of a plural kinds of units, and is introduced in the range of 40 to 90 mole % based on the amount of the whole repeating unit of the polymer according to the present invention. Provided that when the unit represented by the formula (5) or the unit represented by the formula (6), or both of them, is/are used, which is/are a unit(s) providing higher etching resistance to the polymer used in the present invention mentioned later, and the unit has a phenolic hydroxyl group as a substituent, the above-mentioned range includes the ratio of the unit(s).

The unit represented by the above-mentioned general formula (3) is a unit in which one or more of the phenolic hydroxyl groups substituted on the aromatic ring of the unit represented by the above-mentioned general formula (4) is protected by an acid-labile group represented by X', or the phenolic hydroxyl group is substituted by a carboxyl group and the carboxylic acid moiety is protected by an acid-labile group represented by X'. Such an acid-labile group may include any of the groups as long as it has been used in the conventionally known large number of the chemically amplified resist compositions, and provides an acidic group eliminated by an acid, without any particular limitation.

It is preferred to carry out protection of the above-mentioned acid-labile group by a tertiary alkyl group since a pattern reduced in roughness (a phenomenon that the edge profile of the pattern becomes irregular profile) such as LER, etc., can be obtained even when the resist film is made a thin film having a thickness of 10 to 100 nm and, for example, a fine pattern having a line width of 45 nm or less is formed. Further, as the tertiary alkyl group to be used at that time is preferably those having 4 to 18 carbon atoms for obtaining a monomer for polymerization by distillation. In addition, the alkyl substituent of the tertiary carbon in the tertiary alkyl group may be mentioned a linear, branched or cyclic alkyl group having 1 to 15 carbon atoms which may partially contain an oxygen-containing functional group such as an ether bond and a carbonyl group, and substituted alkyl groups with tertiary carbon may be bonded to each other to form a ring.

Preferred examples of the above-mentioned alkyl substituent may be mentioned a methyl group, an ethyl group, a propyl group, an adamantyl group, a norbornyl group, a tetrahydrofuran-2-yl group, a 7-oxanorbornane-2-yl group, a cyclopentyl group, a 2-tetrahydrofuryl group, a tricyclo [5.2.1.0$^{2,6}$]decyl group, a tetracyclo[4.4.0.1$^{2,5}$, 1$^{7,10}$]dodecyl group and a 3-oxo-1-cyclohexyl group. Also, as the tertiary alkyl group having the above as the substituent(s), there may be specifically exemplified by a t-butyl group, a t-pentyl group, a 1-ethyl-1-methylpropyl group, a 1,1-diethylpropyl group, a 1,1,2-trimethylpropyl group, a 1-adamantyl-1-methylethyl group, a 1-methyl-1-(2-norbornyl)ethyl group, a 1-methyl-1-(tetrahydrofuran-2-yl)ethyl group, a 1-methyl-1-(7-oxanorbornane-2-yl)ethyl group, a 1-methylcyclopentyl group, a 1-ethylcyclopentyl group, a 1-propylcyclopentyl group, a 1-cyclopentylcyclopentyl group, a 1-cyclohexylcyclopentyl group, a 1-(2-tetrahydrofuryl)cyclopentyl group, a 1-(7-oxanorbornane-2-yl)cyclopentyl group, a 1-methylcyclohexyl group, a 1-ethylcyclohexyl group, a 1-cyclopentylcyclohexyl group, a 1-cyclohexylcyclohexyl group, a 2-methyl-2-norbornyl group, a 2-ethyl-2-norbornyl group, a 8-methyl-8-tricyclo[5.2.1.0$^{2,6}$]decyl group, a 8-ethyl-8-tricyclo[5.2.1.0$^{2,6}$]decyl group, a 3-methyl-3-tetracyclo [4.4.0.1$^{2,5}$, 1$^{7,10}$]dodecyl group, a 3-ethyl-3-tetracyclo [4.4.0.1$^{2,5}$, 1$^{7,10}$]dodecyl group, a 2-methyl-2-adamantyl group, a 2-ethyl-2-adamantyl group, a 1-methyl-3-oxo-1-cyclohexyl group, a 1-methyl-1-(tetrahydrofuran-2-yl)ethyl group, a 5-hydroxy-2-methyl-2-adamantyl group and a 5-hydroxy-2-ethyl-2-adamantyl group, but the invention is not limited by these.

Also, the acetal group represented by the following general formula (15) is a useful option as the acid-labile group which is frequently utilized as an acid-labile group, and stably provides a pattern in which an interface between the pattern and the substrate is relatively rectangular,

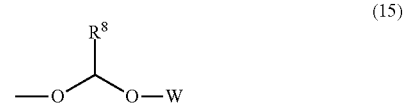

(15)

wherein R$^8$ represents a hydrogen atom, or a linear, branched or cyclic alkyl group having 1 to 10 carbon atoms, and W represents a linear, branched or cyclic alkyl group having 1 to 30 carbon atoms.

Among the above-mentioned acetal group, it is particularly preferred to contain a polycyclic alkyl group having 7 to 30 carbon atoms as W for the purpose of obtaining higher resolution. Also, when W contains a polycyclic alkyl group, it is preferred that a bond is formed between the secondary carbon constituting the polycyclic ring structure and the acetal oxygen. The bond is preferably formed on the secondary carbon of the cyclic structure than the case where the bond is formed on the tertiary carbon of the same since the polymer becomes a more stable compound, storage stability becomes good as a resist composition, and resolution deterioration is not caused. Also, when the bond is formed on the secondary carbon, it is preferred as compared with the case where W is bonded onto a primary carbon interposed by a linear alkyl group having 1 or more carbon atoms, since the glass transition temperature (Tg) of the polymer becomes good and the poor profile of the resist pattern after development is not caused by baking.

Incidentally, specific examples of the above-mentioned general formula (15) may be exemplified by the following,

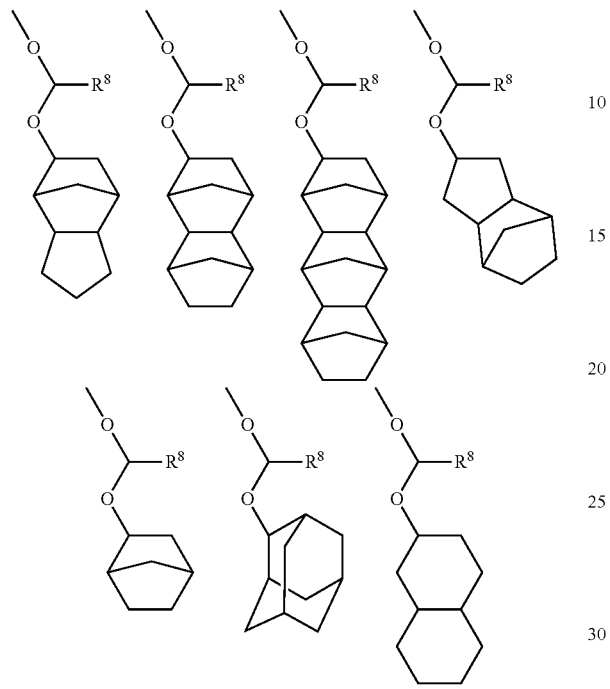

wherein $R^8$ has the same meaning as defined above.

In the above-mentioned general formulae, $R^8$ represents a hydrogen atom or a linear, branched or cyclic alkyl group having 1 to 10 carbon atoms, and optionally selected depending on the design of sensitivity of the decomposable group to the acid. For example, if the design is to decompose the group by a strong acid while ensuring relatively high stability, then, a hydrogen atom is selected, and if the design is to obtain higher sensitivity to pH change using a group having relatively high reactivity, then, a linear alkyl group is selected. While it may vary depending on the combination of an acid generator and a basic compound to be formulated in the resist composition, when it is designed that a relatively bulky alkyl group as mentioned above is substituted at the terminal, and solubility change by decomposition is made large, a group in which the carbon having a bond with the acetal carbon is a secondary carbon is preferred as $R^8$. Examples of $R^8$ to be bonded to the acetal carbon with the secondary carbon may be mentioned an isopropyl group, a sec-butyl group, a cyclopentyl group, a cyclohexyl group, etc.

As the selection of the other acid-labile groups, a selection that a (—$CH_2COO$-tertiary alkyl group) is bonded to the phenolic hydroxyl group may be carried out. As the tertiary alkyl group to be used in this case, the same tertiary alkyl group as that to be used for protection of the above-mentioned phenolic hydroxyl group may be used.

The unit represented by the above-mentioned general formula (3), protected by the acid-labile group, and became alkali soluble by the action of an acid may be used one kind alone, or may be used in combination of a plural kinds of units, and preferably introduced in the range of 5 to 45 mole % based on the amount of the whole repeating unit of the polymer.

It is also preferred that the above-mentioned base resin contains a repeating unit represented by the following general formula (5) or a repeating unit represented by the following general formula (6), or both of them,

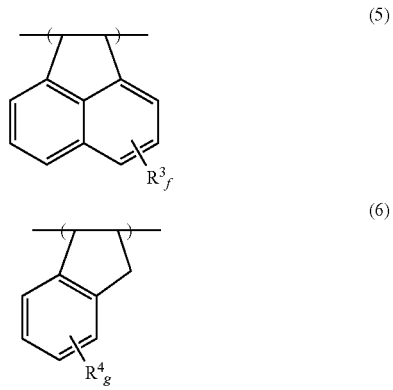

wherein "f" represents an integer of 0 to 6; each $R^3$ independently represents a hydrogen atom, an alkyl group having 1 to 6 carbon atoms which may be substituted by a halogen atom(s), a primary or secondary alkoxy group which may be substituted by a halogen atom(s), or an alkylcarbonyloxy group having 1 to 7 carbon atoms which may be substituted by a halogen atom(s); "g" represents an integer of 0 to 4; each $R^4$ independently represents a hydrogen atom, an alkyl group having 1 to 6 carbon atoms which may be substituted by a halogen atom(s), a primary or secondary alkoxy group which may be substituted by a halogen atom(s), or an alkylcarbonyloxy group having 1 to 7 carbon atoms which may be substituted by a halogen atom(s).

When these repeating units (the repeating unit represented by the above-mentioned general formula (5) or the repeating unit represented by the above-mentioned general formula (6) or both of them) are used as a constitutional component(s), it is possible to obtain an effect of heightening resistance to electron beam irradiation at the time of etching or pattern inspection due to addition of the cyclic structure to the main chain, in addition to etching resistance due to the aromatic ring.

The above-mentioned repeating unit which provides a cyclic structure to the main chain to improve etching resistance may be used one kind alone, or may be used in combination of a plural kinds of units, and it is preferably introduced with 5 mole % or more based on the amount of the whole monomer unit constituting the polymer for the purpose of obtaining the effect that etching resistance is improved. In the case that the unit has a polarity by the action of the functional group contained in the cyclic structure and gives adhesion to the substrate, or the unit has the substituent which is protected by the above-mentioned acid-labile group, and becomes alkali soluble by the action of an acid, the amount of the repeating unit to be introduced is added to the above-mentioned respective preferred ranges. When the unit does not have a functional group, or the functional group does not correspond to any of the cases, the amount is preferably 30 mole % or less. If the introducing amount of the case where the unit does not have a functional group, or the functional group does not correspond to any of the cases is 30 mole % or less, it is preferred since there is no fear of causing development defects.

The base resin to be used in the chemically amplified resist composition of the present invention preferably comprises the units of the above-mentioned general formulae (3) and (4) as the main constitutional units, and further the units of the formulae (5) and (6) which can be introduced, in an amount of 60 mole % or more based on the amount of the whole monomer unit constituting the base resin whereby the characteristics of the chemically amplified resist composition of the present invention can be certainly obtained, more preferably 70 mole % or more, particularly preferably 85 mole % or more.

When the base resin comprises the repeating units(s) selected from the units represented by the formulae (3) to (6) as the whole constitutional unit, both high etching resistance and excellent resolution can be attained. As the repeating units other than the units represented by the formulae (3) to (6), there may be used a (meth)acrylate ester unit protected by the conventionally used acid-labile group, or a (meth)acrylate ester unit having an adhesion group such as a lactone structure, etc. Fine adjustment of the characteristics of the resist film may be carried out by these other repeating unit(s), but these unit(s) may not be contained.

The base resin to be used in the resist composition of the present invention can be obtained by copolymerizing the respective monomers by combining protection and deprotection reaction, depending on necessity, according to the conventionally known method. The copolymerization reaction is not particularly limited, and preferably radical polymerization, or anion polymerization. These methods can be referred to International Patent Laid-Open Publication No. 2006/121096, Japanese Patent Laid-Open Publication No. 2008-102383, Japanese Patent Laid-Open Publication No. 2008-304590, and Japanese Patent Laid-Open Publication No. 2004-115630.

A preferred molecular weight of the above-mentioned base resin to be used in the above-mentioned chemically amplified positive resist composition is preferably a weight average molecular weight of 2,000 to 50,000, more preferably 3,000 to 20,000 when the molecular weight is measured, as a general method, by gel permeation chromatography (GPC) using polystyrenes as standard samples. If the weight average molecular weight is 2,000 or more, there is no fear of causing the phenomenon that the profile of the pattern becomes rounding to lower the resolution, as well as the line edge roughness is deteriorated as has conventionally been known. On the other hand, if the molecular weight becomes larger than required, line edge roughness tends to be increased while it depends on the pattern to be resolved, so that the molecular weight is preferably controlled to 50,000 or less, in particular, when a pattern with a pattern line width of 100 nm or less is to be formed, it is preferably controlled to 20,000 or less.

Incidentally, measurement of the GPC can be carried out by using tetrahydrofuran (THF) solvent generally used.

Further, in the base resin to be used in the above-mentioned chemically amplified resist composition of the present invention, the molecular weight distribution (Mw/Mn) is preferably narrow distribution of 1.0 to 2.0, in particular 1.0 to 1.8. When it is narrow distribution as mentioned above, no foreign substance is generated on the pattern or the profile of the pattern is not deteriorated after development.

In the chemically amplified resist composition of the present invention, a photoacid generator, i.e., or a compound generating an acid in response to active beam or radiation beam may be contained to cause to function the chemically amplified positive resist composition to be used in the patterning process of the present invention. As the component of the photoacid generator, any compound may be used so long as it is a compound generating an acid by irradiation of high-energy beam. Suitable photoacid generator may be mentioned a sulfonium salt, an iodonium salt, sulfonyldiazomethane, N-sulfonyloxyimide, oxime-O-sulfonate type acid generator, etc. These may be used singly or in admixture of two or more kinds.

Specific examples of such a photoacid generator are disclosed in the paragraphs [0122] to [0142] of Japanese Patent Laid-Open Publication No. 2008-111103.

Among the specific examples of the above-mentioned photoacid generator, an arylsulfonate type photoacid generator is preferred to generate an acid with suitable acid strength.

The chemically amplified resist composition of the present invention may contain a basic compound. By adding the basic compound, acid diffusion can be effectively controlled, and even when a substrate having a layer containing chromium at the outermost layer is used as the workpiece, an effect of the acid generated in the resist film onto the layer containing chromium can be suppressed. An amount of the basic compound to be added is preferably 0.01 to 5 parts by mass, particularly 0.05 to 3 parts by mass based on 100 parts by mass of the above-mentioned polymer. In addition, a large number of the basic compounds which can be used has been known, and primary, secondary and tertiary aliphatic amines, mixed amines, aromatic amines, heterocyclic amines, a nitrogen-containing compound having a carboxyl group, a nitrogen-containing compound having a sulfonyl group, a nitrogen-containing compound having a hydroxyl group, a nitrogen-containing compound having a hydroxyphenyl group, an alcoholic nitrogen-containing compound, amides, imides, carbamates, ammonium salts, etc., have been known. These specific examples have been exemplified in Patent Document 6 with a large number, and all of these can be basically used, and two or more basic compounds may be selected and used in admixture.

A particularly preferably formulated basic compound may be mentioned tris(2-(methoxymethoxy)ethyl)amine, tris(2-(methoxymethoxy)ethyl)amine N-oxide, morpholine derivatives, imidazole derivatives, etc.

To the chemically amplified positive resist composition of the present invention may be added an organic solvent for improving coating property to the workpiece, etc. Specific examples of the organic solvent may be exemplified by those disclosed at the paragraph [0144] of Japanese Patent Laid-Open Publication No. 2008-111103.

A formulation amount of the organic solvent is preferably 200 to 3,000 parts by mass based on 100 parts by mass of the base resin, and particularly 400 to 2,500 parts by mass are suitable.

To the chemically amplified positive resist composition of the present invention may be added a surfactant commonly used for improving coating property. When the surfactant is used, a lot of surfactants have been conventionally known as many examples are disclosed in International Patent Laid-Open Publication No. 2006/121096, Japanese Patent Laid-Open Publication No. 2008-102383, Japanese Patent Laid-Open Publication No. 2008-304590, Japanese Patent Laid-Open Publication No. 2004-115630 and Japanese Patent Laid-Open Publication No. 2005-8766, and a suitable surfactant can be selected by referring to these.

An amount of the surfactant to be added is preferably 2 parts by mass or less, more preferably 1 part by mass or less and 0.01 part by mass or more based on 100 parts by mass of the base polymer in the chemically amplified resist composition.

When such a chemically amplified positive resist composition is employed, acid diffusion at the time of exposure can be effectively controlled by the action of the onium salt, and it has adhesion to the workpiece and good etching selectivity to the workpiece so that a pattern which is fine and having high resolution, and reduced in LER can be obtained.

[Patterning Process]

The present invention is further to provide a patterning process which comprises the steps of forming a resist film on a workpiece using the above-mentioned chemically amplified positive resist composition, irradiating a high-energy beam to the resist film, and developing the resist film after irradiation using an alkaline developer to obtain a resist pattern.

In the patterning process of the present invention, a pattern can be formed by employing the conventionally known lithography technology. Generally, the above-mentioned chemically amplified positive resist composition is coated on a workpiece exemplified by a substrate (Si, $SiO_2$, SiN, SiON, TiN, WSi, BPSG, SOG, an organic anti-reflecting film, etc.) for manufacturing an integrated circuit or a substrate (Cr, CrO, CrON, MoSi, etc.) for manufacturing a mask circuit, etc., by the means of spin coating, etc., so as to make a film thickness of 0.05 to 2.0 μm, and the film is prebaked on a hot plate at 60 to 150° C. for 1 to 20 minutes, preferably at 80 to 140° C. for 1 to 10 minutes to form a resist film.

Then, by using a mask for forming an objective pattern, or directly by beam exposure, a high-energy beam such as ultraviolet beam, far ultraviolet beam, electron beam, EUV, X ray, y beam, synchrotron radiation ray, etc., is pattern irradiated with an exposure dose of 1 to 200 $mJ/cm^2$, preferably 10 to 100 $mJ/cm^2$. Incidentally, the chemically amplified positive resist composition of the present invention is particularly effective in the case of pattern irradiation using EUV or an electron beam. Exposure may be carried out by the usual exposure method as well as, in some cases, the immersion method in which immersion is carried out between the mask and the resist. In such a case, it is possible to use a top coat insoluble with water.

Next, the film is subjected to post-exposure bake (PEB) on a hot plate at 60 to 150° C. for 1 to 20 minutes, preferably at 80 to 140° C. for 1 to 10 minutes. Further, by using a developer of an aqueous alkali solution containing 0.1 to 5% by mass, preferably 2 to 3% by mass of tetramethylammonium hydroxide (TMAH), etc., development is carried out by the conventional method such as a dipping method, a puddle method, a spray method, etc., for 0.1 to 3 minutes, preferably for 0.5 to 2 minutes, to form an objective pattern on the substrate.

Incidentally, the resist composition of the present invention has particularly high etching resistance, and the composition is useful when it is used under the conditions that require small change in pattern line width even when the time to the post-exposure baking after exposure is elongated. Also, it is particularly useful, as a substrate to be processed, for a substrate having a material which likely causes pattern peeling-off or pattern fall on the surface thereof by the reason that adhesion of the resist pattern is poor, and is useful for forming a pattern on a substrate on which a film is formed by sputtering metal chromium or a chromium compound containing one or more light elements such as oxygen, nitrogen and carbon at the outermost surface as a layer, in particular, on a photomask blank.

Such a patterning process is employed, by using the above-mentioned chemically amplified positive resist composition for forming a resist film, acid diffusion at the time of exposure can be effectively controlled, and even when a substrate (in particular, a photomask blank) having a layer containing chromium at the outermost surface is used as a workpiece, an effect of a generating acid can be suppressed, so that a pattern having high resolution and reduced in LER can be formed. In addition, adhesion between the resist film and the workpiece as well as etching selectivity are good, and occurrence of pattern fall or poor pattern transferring, etc. can be suppressed when a micro pattern is formed thinning of the resist film, so that it can be suitably used for microprocessing technology, in particular, for an electron beam, EUV lithography technology.

EXAMPLES

In the following, the present invention is specifically explained by referring to Synthesis Examples, Examples and Comparative Example, but the present invention is not limited by the following Examples. Incidentally, in the following examples, Me represents a methyl group. Also, the copolymerization composition ratio is a molar ratio, and the weight average molecular weight (Mw) shows a weight average molecular weight in terms of a polystyrene by gel permeation chromatography (GPC).

Synthesis Example 1

Synthesis of Onium Salt

The onium salt of the present invention was synthesized by the scheme mentioned below. The structure of the synthesized onium salts (Q-1 to Q-4) of the present invention and the structure of the onium salts (Comparative Q-1 to Q-4) to be used in Comparative Examples were shown in Table 5 mentioned later.

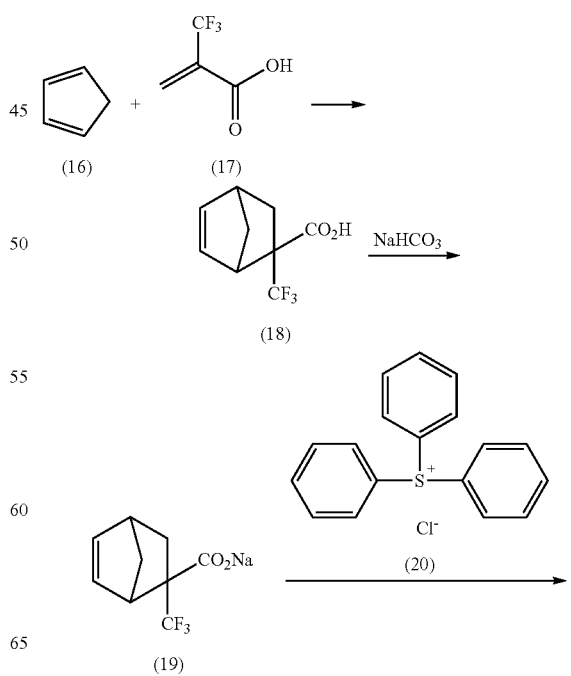

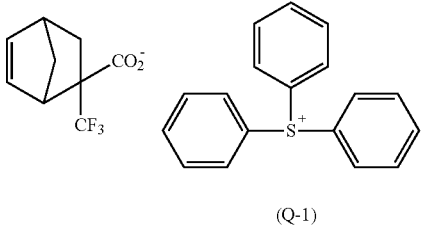

(Q-1)

Synthesis Example 1-1

Synthesis of Q-1

Synthesis Example 1-1-1

Synthesis of 2-trifluoromethylbicyclo[2,2,1]hepta-5-ene-2-carboxylic acid (18)

22.7 g of cyclopentadiene (16) and 40.0 g of trifluoromethylacrylic acid (17) were stirred at room temperature in 40 g of benzene overnight. 20 g of hexane was poured into the reaction mixture to precipitate white solid and the precipitate was collected by filtration to obtain 45.6 g (Yield: 77%) of the carboxylic acid (18).

Synthesis Example 1-1-2

Synthesis of sodium 2-trifluoromethylbicyclo[2,2,1]hepta-5-ene-2-carboxylate (19)

5.0 g of the carboxylic acid (18) obtained in (Synthesis Example 1-1-1) was dissolved in 10.0 g of methylene chloride, and 2.0 g of sodium hydrogen carbonate and 10 g of water were added to the solution and the resulting mixture was stirred overnight. Methylene chloride and water were distilled off under reduced pressure to obtain sodium carboxylate (19). This material was used in the next reaction without purification any more.

Synthesis Example 1-1-3

Synthesis of triphenylsulfonium 2-trifluoromethylbicyclo[2,2,1]hepta-5-ene-2-carboxylate (Q-1)

Sodium carboxylate (19) obtained in (Synthesis Example 1-1-2) was dissolved in 20 g of methylene chloride, 40 g of an aqueous solution of triphenylsulfonium chloride (20) was added to the solution and the resulting mixture was, stirred for 30 minutes. The organic layer was separated, the aqueous layer was extracted with $CH_2Cl_2$, and the combined organic layers were washed three times with $H_2O$. The solvent was distilled off under reduced pressure to obtain 4.6 g of the objective material, onium salt (Q-1) (Yield: 40%).

Synthesis Example 1-2

Synthesis of Q-2

Synthesis was carried out in the same manner except for changing cyclopentadiene in the synthesis of Q-1 in Synthesis Example 1-1 to furan to obtain 3.8 g (three-step yield: 29%) of Q-2.

Synthesis Example 1-3

Synthesis of Q-3

2-Trifluoromethylbicyclo[2,2,1]hepta-5-ene-2-carboxylic acid (18) obtained in Synthesis Example 1-1-1 was stirred in a toluene solvent in the presence of 5% Pd/C catalyst at room temperature under hydrogen atmosphere to obtain 2-trifluoromethylbicyclo[2,2,1]heptane-2-carboxylic acid. In the same synthetic routes as in Synthesis Example 1-1-2 to 1-1-3 except for using the carboxylic acid as the starting material to obtain 3.9 g (four-step yield: 32%) of Q-3.

Synthesis Example 1-4

Synthesis of Q-4

In the same synthetic routes as in Synthesis Example 1-1-2 to 1-1-3 except for changing the carboxylic acid (18) in Synthesis Example (1-1-2) to the carboxylic acid represented by the following general formula (21) to obtain 2.8 g (two-step yield: 33%) of Q-4.

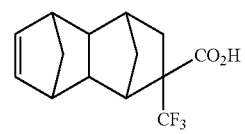

(21)

Synthesis Example 2

Synthesis of Base Resin

The base resins (polymers) used in the resist compositions of the present invention were synthesized by the following scheme. The composition ratios of the synthesized respective polymers were shown in Table 1, and the structures of the repeating units were shown in Table 2 to Table 4.

Polymer Synthesis Example 2-1

Synthesis of Polymer 1

To 3 L of a flask were added 407.5 g of acetoxy-styrene, 42.5 g of acenaphthylene, and 1,275 g of toluene as a solvent. The reaction apparatus was cooled to −70° C. under nitrogen atmosphere, and degassing under reduced pressure and nitrogen flow were repeated three times. After the temperature was raised to room temperature, 34.7 g of 2,2'-azobis(2,4-dimethylvaleronitrile) (V-65 available from Wako Pure Chemical Industries, Ltd.) was added to the mixture as a polymerization initiator, and after the temperature was raised to 55° C., the reaction was carried out for 40 hours. To the reaction solution was added dropwise a mixed solution comprising 970 g of methanol and 180 g of water under stirring. After 30 minutes, the lower layer (polymer layer) was concentrated under reduced pressure, the polymer layer was dissolved again in 0.45 L of methanol and 0.54 L of tetrahydrofuran, then, 160 g of triethylamine and 30 g of water were added to the mixture, and the resulting mixture was heated to 60° C. to carry out deprotecting reaction for 40 hours. The solution subjected to deprotecting reaction was concentrated under reduced pressure, and the concentrate was dissolved in 548 g of methanol and 112 g of acetone. To the solution was added dropwise 990 g of hexane under stirring, and after 30 minutes, 300 g of tetrahydrofuran was added to the lower layer (polymer layer). To the resulting mixture was added dropwise 1030 g of hexane under stirring, and after 30 minutes, the lower layer (polymer layer) was concentrated under reduced pressure. This polymer solution was neutralized by using 82 g of acetic acid, the reaction solution was concentrated and the concentrate was dissolved in 0.3 L of acetone, precipitated in 10 L of water, and the precipitate was collected by filtration and dried to obtain 280 g of white polymer. The obtained polymer was measured by $^1$H-NMR and GPC, and the following analytical results were obtained.

Copolymerization composition ratio

Hydroxystyrene:acenaphthylene=89.3:10.7

Weight average molecular weight (Mw)=5000

Molecular weight distribution (Mw/Mn)=1.63

With 100 g of the obtained polymer was reacted 50 g of (2-methyl-1-propenyl)methyl ether under acidic conditions, and the reaction mixture was subjected to neutralization, separation of the liquids and crystallization to obtain Polymer 1. Yield was 125 g. This is called (Polymer 1).

Polymer 1

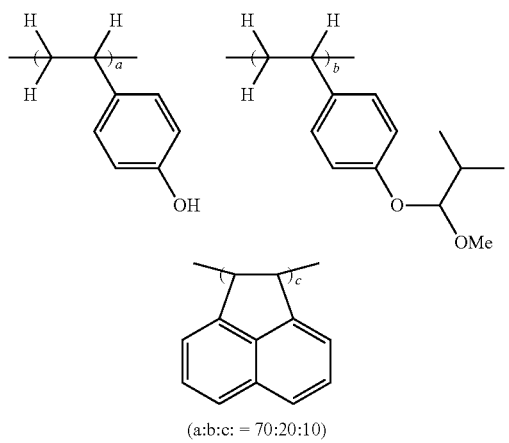

(a:b:c = 70:20:10)

Polymer Synthesis Example 2-2

Synthesis of Polymer 2

Synthesis was carried out in the same manner as in Polymer Synthesis Example 2-1 except for changing (2-methyl-1-propenyl)methyl ether in Polymer Synthesis Example 2-1 to (2-methyl-1-propenyl)-8-(tricyclo[5,2,1,0$^{2,6}$]decanyl ether to obtain Polymer 2.

Polymer Synthesis Example 2-3

Synthesis of Polymer 3

Synthesis was carried out in the same manner as in Polymer Synthesis Example 2-1 except for changing (2-methyl-1-propenyl)methyl ether in Polymer Synthesis Example 2-1 to (2-methyl-1-propenyl)-2-adamantyl ether to obtain Polymer 3.

Polymer Synthesis Example 2-4

Synthesis of Polymer 4

Into a cylinder for dropping which had been made under a nitrogen atmosphere were charged 362 g of 4-hydroxyphenyl methacrylate, 38.2 g of acenaphthylene, 40.9 g of dimethyl 2,2'-azobis(2-methylpropionate) (=V-601) and 500 g of methyl ethyl ketone to prepare a monomer solution. Into a separate flask for polymerization which had been made under a nitrogen atmosphere was charged 250 g of methyl ethyl ketone, the solvent was heated to 80° C. under stirring, and the above-mentioned monomer solution was added dropwise thereinto over 4 hours. After completion of the dropwise addition, stirring was continued for 4 hours while maintaining the temperature of the polymerization solution to 80° C., and then, cooled to room temperature. The obtained polymerization solution was added dropwise to 10 kg of a hexane/diisopropyl ether solution, and the precipitated copolymer was collected by filtration. The copolymer was washed twice with 5 kg of hexane, and vacuum dried at 50° C. for 20 hours to obtain white powder solid polymer. With 100 g of the obtained polymer was reacted 40.5 g of (2-methyl-1-propenyl)methyl ether under acidic conditions, and the mixture was subjected to neutralization, separation of the liquids and crystallization to obtain Polymer 4. Yield was 128 g.

Polymer Synthesis Example 2-5

Synthesis of Polymer 5

Synthesis was carried out in the same manner as in Polymer Synthesis Example 2-4 except for changing (2-methyl-1-propenyl)methyl ether in Polymer Synthesis Example 2-4 to (2-methyl-1-propenyl)-8-(tricyclo[5,2,1,0$^{2,6}$]decanyl ether to obtain Polymer 5.

Polymer Synthesis Example 2-6

Synthesis of Polymer 6

Synthesis was carried out in the same manner as in Polymer Synthesis Example 2-4 except for changing (2-methyl-1-propenyl)methyl ether in Polymer Synthesis Example 2-4 to (2-methyl-1-propenyl)-2-adamantyl ether to obtain Polymer 6.

Polymer Synthesis Examples 2-7 to 2-12

Syntheses of Polymers 7 to 12

In the case of the polymers containing a hydroxystyrene unit, the resins shown in Table 1 were manufactured in the same manner as in Polymer Synthesis Examples 2-1, 2-2 and 2-3 except for changing the kind and the formulation ratio of the respective monomers. Also, in the case of the polymers containing a 4-hydroxyphenyl methacrylate unit, the resins shown in Table 1 were manufactured in the same manner as in Polymer Synthesis Examples 2-4, 2-5 and 2-6 except for changing the kind and the formulation ratio of the respective monomers.

Polymer Synthesis Example 2-13

Synthesis of Polymer 13

Into a cylinder for dropping which had been made under a nitrogen atmosphere were charged 42.4 g of 4-hydroxyphenyl methacrylate, 40.6 g of 5-oxo-4-oxatricyclo[4.2.1.0$^{3,7}$]nonane-2-yl methacrylate, 16.9 g of 1-methoxy-2-methyl-1-propyl methacrylate, 9.3 g of dimethyl 2,2'-azobis(2-methylpropionate) (=V-601) and 124 g of methyl ethyl ketone to prepare a monomer solution. Into a separate flask for polymerization which had been made under a nitrogen atmosphere was charged 62 g of methyl ethyl ketone, the solvent was heated to 80° C. under stirring, and the above-mentioned monomer solution was added dropwise thereinto over 4 hours. After completion of the dropwise addition, stirring was continued for 4 hours while maintaining the temperature of the polymerization solution to 80° C., and then, cooled to room temperature. The obtained polymerization solution was added dropwise to 1.5 kg of a hexane/diisopropyl ether solution, and the precipitated copolymer was collected by filtration. The copolymer was washed twice with 300 g of hexane, and vacuum dried at 50° C. for 20 hours to obtain white powder solid polymer.

Polymer Synthesis Examples 2-14, 15 and 16

Syntheses of Polymers 14, 15 and 16

The resins shown in Table 1 were manufactured in the same manner as in Polymer Synthesis Example 2-13 except for changing the kind and the formulation ratio of the respective monomers.

The structures of each unit in Table 1 are shown in Tables 2 to 4. Incidentally, in the following Table 1, the introducing ratio shows a molar ratio.

TABLE 1

|  | Unit 1 | Introducing ratio (mole %) | Unit 2 | Introducing ratio (mole %) | Unit 3 | Introducing ratio (mole %) |
|---|---|---|---|---|---|---|
| Polymer 1 | A-1 | 70.0 | B-1 | 20.0 | C-1 | 10.0 |
| Polymer 2 | A-1 | 78.0 | B-3 | 12.0 | C-1 | 10.0 |
| Polymer 3 | A-1 | 79.0 | B-5 | 11.0 | C-1 | 10.0 |
| Polymer 4 | A-2 | 67.0 | B-2 | 23.0 | C-1 | 10.0 |
| Polymer 5 | A-2 | 76.0 | B-4 | 14.0 | C-1 | 10.0 |
| Polymer 6 | A-2 | 77.0 | B-6 | 13.0 | C-1 | 10.0 |
| Polymer 7 | A-1 | 68.0 | B-1 | 22.0 | C-2 | 10.0 |
| Polymer 8 | A-1 | 76.0 | B-3 | 14.0 | C-2 | 10.0 |
| Polymer 9 | A-1 | 77.0 | B-5 | 13.0 | C-2 | 10.0 |
| Polymer 10 | A-2 | 64.0 | B-2 | 26.0 | C-2 | 10.0 |
| Polymer 11 | A-2 | 73.0 | B-4 | 17.0 | C-2 | 10.0 |
| Polymer 12 | A-2 | 74.0 | B-6 | 16.0 | C-2 | 10.0 |
| Polymer 13 | A-2 | 46.0 | B-7 | 19.0 | C-3 | 35.0 |
| Polymer 14 | A-2 | 50.0 | B-8 | 15.0 | C-3 | 35.0 |
| Polymer 15 | A-2 | 50.0 | B-9 | 15.0 | C-3 | 35.0 |
| Polymer 16 | A-1 | 67.0 | B-10 | 23.0 | C-1 | 10.0 |

TABLE 2

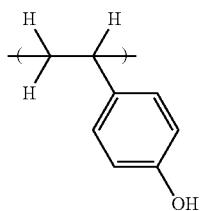

A-1

TABLE 2-continued

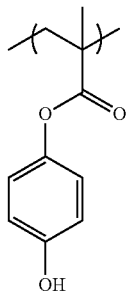

A-2

TABLE 3

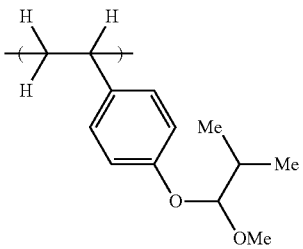 [SMILES: CCC(C)c1ccc(OC(OC)C(C)C)cc1]

B-1

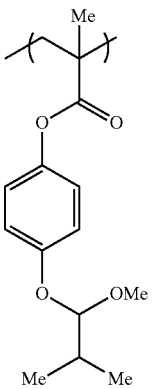

B-2

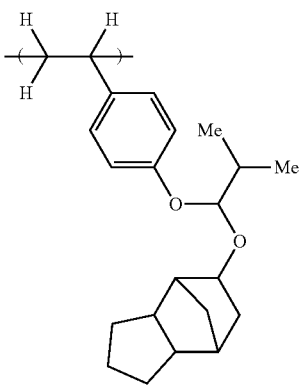 [SMILES: CCC(C)c1ccc(OC(OC2CC3CC2C2CCCC32)C(C)C)cc1]

B-3

TABLE 3-continued
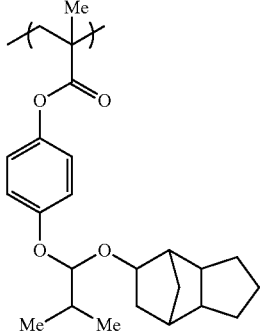
B-4
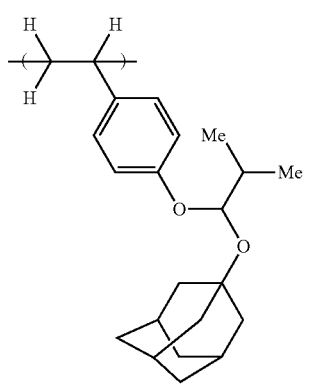 [SMILES: CCC(C)c1ccc(OC(OC23CC4CC(CC(C4)C2)C3)C(C)C)cc1]
B-5
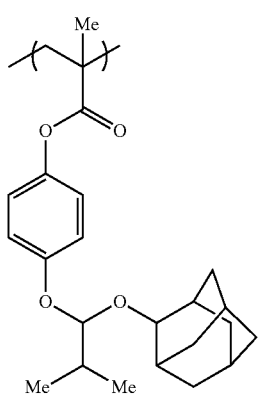
B-6
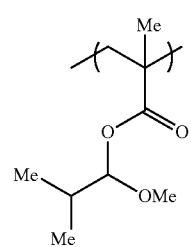
B-7
TABLE 3-continued
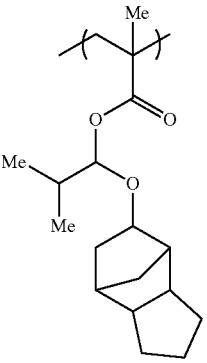
B-8
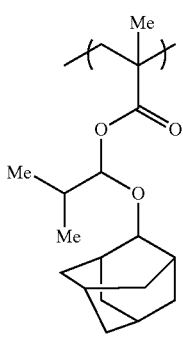
B-9
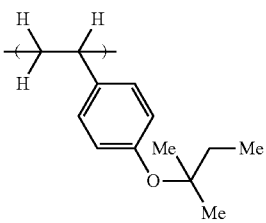 [SMILES: CCC(C)c1ccc(OC(C)(C)CC)cc1]
B-10
TABLE 4
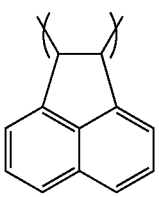
C-1
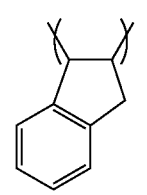
C-2

TABLE 4-continued

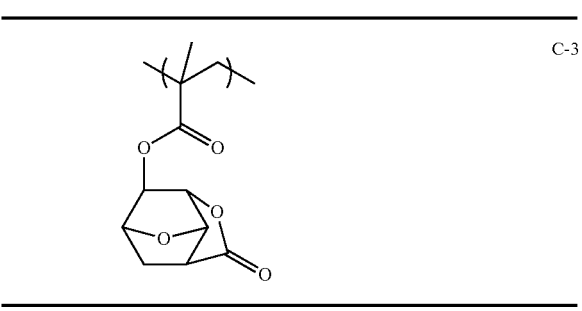

C-3

Preparation of Positive Resist Compositions

The onium salts (Q-1 to Q-4) synthesized as mentioned above, the onium salts for comparative purpose (Comparative Q-1 to Comparative Q-4), the polymers (Polymer 1 to Polymer 16), and photoacid generators (PAG-1, PAG-2) the structures of which are shown below were dissolved in organic solvents with the compositions shown in Table 6 to prepare respective resist compositions, and further the respective compositions were filtered through a 0.2 μm size filter or a 0.02 μm size Nylon or UPE filter to prepare solutions of positive resist compositions, respectively. Also, the structures of the used onium salts and the onium salts for comparison are shown in the following Table 5.

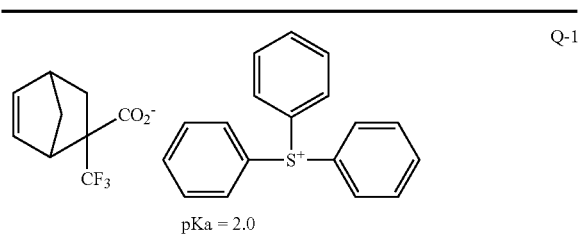

(PAG-1)

(PAG-2)

TABLE 5

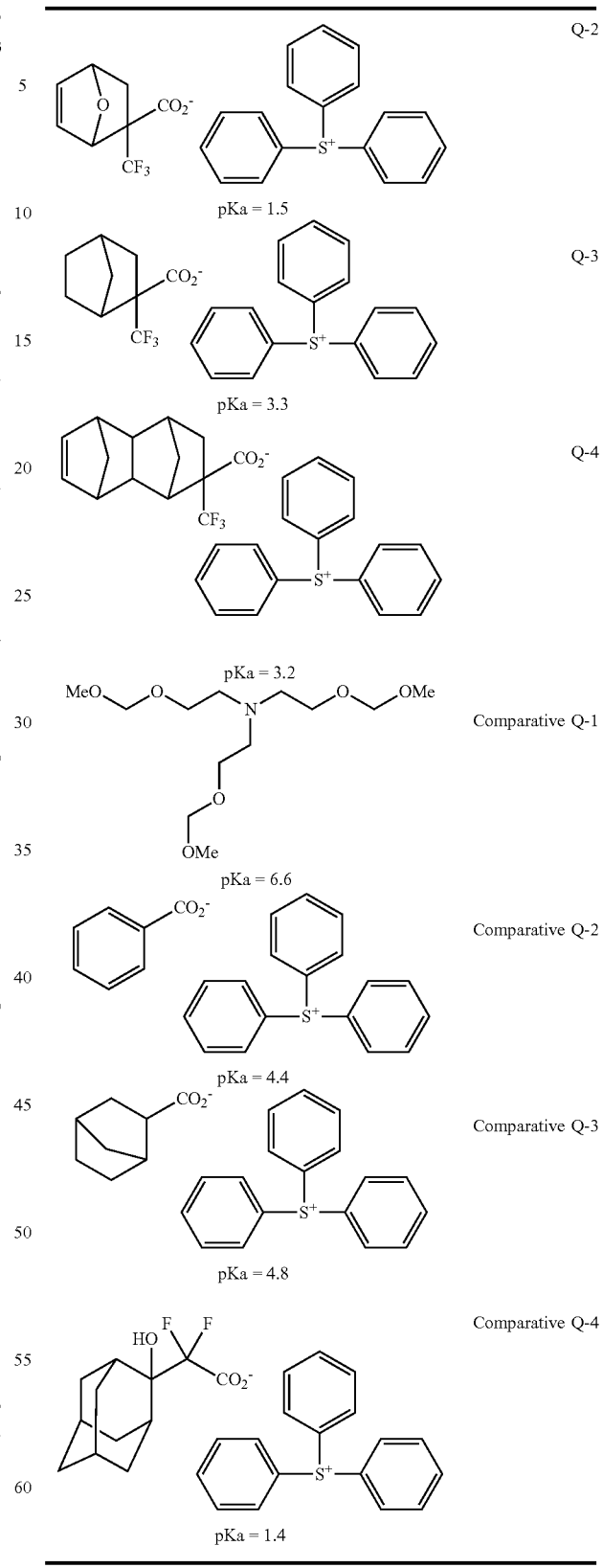

The organic solvents in Table 6 are PGMEA (propylene glycol monomethyl ether acetate), EL (ethyl lactate), PGME (propylene glycol monomethyl ether) and CyH (cyclohexanone). In addition, to the compositions of the respective examples was each added 0.075 part by mass of PF-636 (available from OMNOVA SOLUTIONS, Inc.) as a surfactant other than those described in Table 6.

TABLE 6

| | Acid diffusion controlling Agent | Resin | Photoacid generator | Solvent 1 | Solvent 2 | Solvent 3 |
|---|---|---|---|---|---|---|
| Example 1 | Q-1 (1.4) | Polymer 1 (80) | PAG-1 (8) | PGMEA (1,000) | EL (1,000) | PGME (1,300) |
| Example 2 | Q-1 (1.7) | Polymer 2 (80) | PAG-1 (8) | PGMEA (1,000) | EL (1,000) | PGME (1,300) |
| Example 3 | Q-1 (1.9) | Polymer 2 (80) | PAG-1 (10) | PGMEA (1,000) | EL (1,000) | PGME (1,300) |
| Example 4 | Q-1 (2.1) | Polymer 2 (80) | PAG-1 (12) | PGMEA (1,000) | EL (1,000) | PGME (1,300) |
| Example 5 | Q-1 (1.6) | Polymer 2 (80) | PAG-2 (8) | PGMEA (1,000) | EL (1,000) | PGME (1,300) |
| Example 6 | Q-1 (1.8) | Polymer 2 (80) | PAG-2 (10) | PGMEA (1,000) | EL (1,000) | PGME (1,300) |
| Example 7 | Q-1 (2.0) | Polymer 2 (80) | PAG-2 (12) | PGMEA (1,000) | EL (1,000) | PGME (1,300) |
| Example 8 | Q-1 (1.7) | Polymer 3 (80) | PAG-1 (8) | PGMEA (1,000) | EL (1,000) | PGME (1,300) |
| Example 9 | Q-1 (1.9) | Polymer 3 (80) | PAG-1 (10) | PGMEA (1,000) | EL (1,000) | PGME (1,300) |
| Example 10 | Q-1 (2.1) | Polymer 3 (80) | PAG-1 (12) | PGMEA (1,000) | EL (1,000) | PGME (1,300) |
| Example 11 | Q-1 (1.6) | Polymer 3 (80) | PAG-2 (8) | PGMEA (1,000) | EL (1,000) | PGME (1,300) |
| Example 12 | Q-1 (1.8) | Polymer 3 (80) | PAG-2 (10) | PGMEA (1,000) | EL (1,000) | PGME (1,300) |
| Example 13 | Q-1 (2.0) | Polymer 3 (80) | PAG-2 (12) | PGMEA (1,000) | EL (1,000) | PGME (1,300) |
| Example 14 | Q-1 (1.4) | Polymer 4 (80) | PAG-1 (8) | PGMEA (1,000) | EL (1,000) | PGME (1,300) |
| Example 15 | Q-1 (1.7) | Polymer 5 (80) | PAG-1 (8) | PGMEA (1,000) | EL (1,000) | PGME (1,300) |
| Example 16 | Q-1 (1.7) | Polymer 6 (80) | PAG-1 (8) | PGMEA (1,000) | EL (1,000) | PGME (1,300) |
| Example 17 | Q-1 (1.4) | Polymer 7 (80) | PAG-1 (8) | PGMEA (1,000) | EL (1,000) | PGME (1,300) |
| Example 18 | Q-1 (1.7) | Polymer 8 (80) | PAG-1 (8) | PGMEA (1,000) | EL (1,000) | PGME (1,300) |
| Example 19 | Q-1 (1.7) | Polymer 9 (80) | PAG-1 (8) | PGMEA (1,000) | EL (1,000) | PGME (1,300) |
| Example 20 | Q-1 (1.4) | Polymer 10 (80) | PAG-1 (8) | PGMEA (1,000) | EL (1,000) | PGME (1,300) |
| Example 21 | Q-1 (1.7) | Polymer 11 (80) | PAG-1 (8) | PGMEA (1,000) | EL (1,000) | PGME (1,300) |
| Example 22 | Q-1 (1.7) | Polymer 12 (80) | PAG-1 (8) | PGMEA (1,000) | EL (1,000) | PGME (1,300) |
| Example 23 | Q-2 (1.7) | Polymer 2 (80) | PAG-1 (8) | PGMEA (1,000) | EL (1,000) | PGME (1,300) |
| Example 24 | Q-2 (1.7) | Polymer 3 (80) | PAG-1 (8) | PGMEA (1,000) | EL (1,000) | PGME (1,300) |
| Example 25 | Q-2 (1.7) | Polymer 8 (80) | PAG-1 (8) | PGMEA (1,000) | EL (1,000) | PGME (1,300) |
| Example 26 | Q-2 (1.7) | Polymer 9 (80) | PAG-1 (8) | PGMEA (1,000) | EL (1,000) | PGME (1,300) |
| Example 27 | Q-3 (1.7) | Polymer 2 (80) | PAG-1 (8) | PGMEA (1,000) | EL (1,000) | PGME (1,300) |
| Example 28 | Q-3 (1.7) | Polymer 3 (80) | PAG-1 (8) | PGMEA (1,000) | EL (1,000) | PGME (1,300) |
| Example 29 | Q-3 (1.7) | Polymer 8 (80) | PAG-1 (8) | PGMEA (1,000) | EL (1,000) | PGME (1,300) |
| Example 30 | Q-3 (1.7) | Polymer 9 (80) | PAG-1 (8) | PGMEA (1,000) | EL (1,000) | PGME (1,300) |
| Example 31 | Q-4 (1.7) | Polymer 2 (80) | PAG-1 (8) | PGMEA (1,000) | EL (1,000) | PGME (1,300) |
| Example 32 | Q-4 (1.7) | Polymer 3 (80) | PAG-1 (8) | PGMEA (1,000) | EL (1,000) | PGME (1,300) |
| Example 33 | Q-4 (1.7) | Polymer 8 (80) | PAG-1 (8) | PGMEA (1,000) | EL (1,000) | PGME (1,300) |
| Example 34 | Q-4 (1.7) | Polymer 9 (80) | PAG-1 (8) | PGMEA (1,000) | EL (1,000) | PGME (1,300) |
| Example 35 | Q-1 (1.4) | Polymer 13 (80) | PAG-1 (8) | PGMEA (800) | CyH (1,600) | PGME (400) |
| Example 36 | Q-1 (1.5) | Polymer 14 (80) | PAG-1 (8) | PGMEA (800) | CyH (1,600) | PGME (400) |
| Example 37 | Q-1 (1.6) | Polymer 15 (80) | PAG-1 (8) | PGMEA (800) | CyH (1,600) | PGME (400) |

TABLE 6-continued

| | Acid diffusion controlling Agent | Resin | Photoacid generator | Solvent 1 | Solvent 2 | Solvent 3 |
|---|---|---|---|---|---|---|
| Example 38 | Q-1 (1.2) | Polymer 16 (80) | PAG-1 (8) | PGMEA (1,000) | EL (1,000) | PGME (1,300) |
| Comparative Example 1 | Comparative Q-1 (1.0) | Polymer 2 (80) | PAG-1 (8) | PGMEA (1,000) | EL (1,000) | PGME (1,300) |
| Comparative Example 2 | Comparative Q-1 (1.0) | Polymer 3 (80) | PAG-1 (8) | PGMEA (1,000) | EL (1,000) | PGME (1,300) |
| Comparative Example 3 | Comparative Q-2 (1.4) | Polymer 2 (80) | PAG-1 (8) | PGMEA (1,000) | EL (1,000) | PGME (1,300) |
| Comparative Example 4 | Comparative Q-2 (1.4) | Polymer 3 (80) | PAG-1 (8) | PGMEA (1,000) | EL (1,000) | PGME (1,300) |
| Comparative Example 5 | Comparative Q-3 (1.4) | Polymer 2 (80) | PAG-1 (8) | PGMEA (1,000) | EL (1,000) | PGME (1,300) |
| Comparative Example 6 | Comparative Q-3 (1.4) | Polymer 3 (80) | PAG-1 (8) | PGMEA (1,000) | EL (1,000) | PGME (1,300) |
| Comparative Example 7 | Comparative Q-4 (1.5) | Polymer 2 (80) | PAG-1 (8) | PGMEA (1,000) | EL (1,000) | PGME (1,300) |
| Comparative Example 8 | Comparative Q-4 (1.5) | Polymer 3 (80) | PAG-1 (8) | PGMEA (1,000) | EL (1,000) | PGME (1,300) |
| Comparative Example 9 | Comparative Q-1 (1.0) | Polymer 13 (80) | PAG-1 (8) | PGMEA (800) | CyH (1,600) | PGME (400) |

Evaluation of Electron Beam Drawing

Examples 1 to 34 and 38, and Comparative Examples 1 to 8

Each of the positive resist composition (Examples 1 to 34 and 38, and Comparative Examples 1 to 8) prepared as mentioned above was spin coated onto a 152-mm square mask blank having a chromium oxynitride film at the outermost surface using ACT-M (manufactured by Tokyo Electron Limited), and pre-baked on a hot plate at 90° C. for 600 seconds to form a resist film with a film thickness of 90 nm. The film thickness of the obtained resist film was measured by using an optical film thickness measurement system Nanospec (manufactured by Nanometrics Inc.). Measurement was made at 81 points on surface of the blank substrate excluding an outer edge part within 10 mm inward from the blank periphery, and an average film thickness and a film thickness range were calculated therefrom.

Further, the coated mask blanks were exposed to electron beam exposure apparatus (EBM-5000plus, accelerating voltage: 50 keV, manufactured by NuFlare Technology Inc.), then, baked at 90° C. for 600 seconds (PEB: post exposure bake), and developed with a 2.38% by mass of tetramethylammonium hydroxide aqueous solution, whereby positive patterns could be obtained. Further, the obtained resist patterns were evaluated as follows.

The prepared patterned mask blank was observed under a top-down scanning electron microscope (SEM), the exposure dose which provided a 1:1 resolution at a 400 nm 1:1 line and space (LS) pattern was defined to be the optimum exposure dose ($\mu C/cm^2$), the minimum dimension at the exposure dose which provided a 1:1 resolution of a 400 nm LS pattern was defined to be the resolution (limiting resolution), and edge roughness of the 200 nm LS pattern was measured by SEM. With regard to the pattern profile, it was judged whether it is rectangular or not with naked eyes. With regard to the adhesion, peeling-off was observed with naked eyes when a top-down observation was carried out by a top-down SEM. Evaluation results of the resist compositions of the present invention and the resist compositions for the comparison in EB drawing were shown in Table 7. The post-exposure delay (PED) under vacuum was evaluated by drawing the blank by an electron beam drawing apparatus, allowing it in the vacuum apparatus for 20 hours, thereafter PEB and development were carried out. The obtained line width at Eop of the 400 nm line and space pattern was compared with the line width of the resist pattern which had been immediately baked after exposure, and the difference was shown with [nm]. In addition, CD uniformity (CDU) was evaluated at 49 points on surface of the blank substrate excluding an outer edge part within 20 mm inward from the blank periphery, by measuring the line width at the exposure dose ($\mu C/cm^2$) which provided a 1:1 resolution at a 400 nm 1:1 line and space pattern, and 3σ value of the value in which each measured point was deducted from the average value of the line width was calculated. Evaluation results of the respective resist compositions are shown in the following Table 7.

TABLE 7

| | Optimum Exposure Dose ($\mu C/cm^2$) | Limiting Resolution (nm) | LER (nm) | CDU (3σ) (nm) | Pattern Profile |
|---|---|---|---|---|---|
| Example 1 | 24 | 45 | 4.9 | 2.6 | Rectangular |
| Example 2 | 25 | 40 | 4.6 | 2.3 | Rectangular |
| Example 3 | 25 | 40 | 4.5 | 2.2 | Rectangular |
| Example 4 | 26 | 40 | 4.7 | 2.5 | Rectangular |
| Example 5 | 25 | 40 | 4.6 | 2.4 | Rectangular |
| Example 6 | 25 | 40 | 4.6 | 2.3 | Rectangular |
| Example 7 | 26 | 40 | 4.5 | 2.3 | Rectangular |
| Example 8 | 26 | 40 | 4.7 | 2.5 | Rectangular |
| Example 9 | 25 | 40 | 4.6 | 2.5 | Rectangular |
| Example 10 | 26 | 40 | 4.5 | 2.2 | Rectangular |
| Example 11 | 25 | 40 | 4.5 | 2.4 | Rectangular |
| Example 12 | 25 | 40 | 4.7 | 2.5 | Rectangular |
| Example 13 | 26 | 40 | 4.6 | 2.3 | Rectangular |
| Example 14 | 25 | 45 | 4.9 | 2.5 | Rectangular |
| Example 15 | 26 | 45 | 4.8 | 2.4 | Rectangular |
| Example 16 | 26 | 45 | 4.8 | 2.5 | Rectangular |
| Example 17 | 25 | 40 | 4.8 | 2.2 | Rectangular |
| Example 18 | 26 | 40 | 4.7 | 2.3 | Rectangular |
| Example 19 | 26 | 40 | 4.7 | 2.4 | Rectangular |
| Example 20 | 25 | 45 | 4.9 | 2.2 | Rectangular |
| Example 21 | 26 | 45 | 4.8 | 2.6 | Rectangular |
| Example 22 | 26 | 45 | 4.8 | 2.2 | Rectangular |
| Example 23 | 25 | 40 | 4.7 | 2.2 | Rectangular |
| Example 24 | 26 | 40 | 4.6 | 2.4 | Rectangular |
| Example 25 | 25 | 40 | 4.7 | 2.3 | Rectangular |
| Example 26 | 26 | 40 | 4.6 | 2.4 | Rectangular |
| Example 27 | 25 | 40 | 4.7 | 2.4 | Rectangular |
| Example 28 | 26 | 40 | 4.6 | 2.3 | Rectangular |

TABLE 7-continued

| | Optimum Exposure Dose (µC/cm²) | Limiting Resolution (nm) | LER (nm) | CDU (3σ) (nm) | Pattern Profile |
|---|---|---|---|---|---|
| Example 29 | 25 | 40 | 4.7 | 2.4 | Rectangular |
| Example 30 | 26 | 40 | 4.6 | 2.3 | Rectangular |
| Example 31 | 25 | 40 | 4.7 | 2.3 | Rectangular |
| Example 32 | 26 | 40 | 4.6 | 2.3 | Rectangular |
| Example 33 | 25 | 40 | 4.7 | 2.4 | Rectangular |
| Example 34 | 26 | 40 | 4.6 | 2.3 | Rectangular |
| Example 38 | 26 | 45 | 4.7 | 2.5 | Rectangular |
| Comparative Example 1 | 24 | 55 | 6.0 | 3.6 | Rectangular |
| Comparative Example 2 | 25 | 55 | 6.0 | 3.6 | Rectangular |
| Comparative Example 3 | 25 | 55 | 5.9 | 3.4 | Rectangular |
| Comparative Example 4 | 26 | 55 | 5.9 | 3.4 | Rectangular |
| Comparative Example 5 | 25 | 55 | 5.9 | 3.4 | Rectangular |
| Comparative Example 6 | 25 | 55 | 5.9 | 3.4 | Rectangular |
| Comparative Example 7 | 10 | 55 | 8.2 | 3.4 | Rectangular |
| Comparative Example 8 | 10 | 55 | 7.8 | 3.4 | Rectangular |

Evaluation of EUV Exposure

Examples 35 to 38, and Comparative Example 9

The positive resist compositions. (Examples 35 to 38, and Comparative Example 9) prepared as mentioned above were each spin coated on an Si substrate having a diameter of 4 inches which had been subjected to the hexamethyldisilazane (HMDS) vapor prime treatment, and pre-baked on a hot plate at 105° C. for 60 seconds to form a resist film with a thickness of 50 nm. This was subjected to EUV exposure with NA0.3 and dipole illumination.

The coated substrate was subjected to post-exposure bake (PEB) for 60 seconds on a hot plate immediately after exposure and to paddle development with 2.38% by mass of TMAH aqueous solution for 30 seconds, whereby the positive pattern was obtained.

The obtained resist pattern was evaluated as follows. The minimum dimension at the exposure dose which provided a 1:1 resolution of a 35 nm LS pattern was defined to be the resolution (limiting resolution), and the edge roughness (LER) of 35 nm LS pattern was measured by SEM. With regard to the pattern profile, it was judged whether it is rectangular or not with naked eyes. With regard to the adhesion, peeling-off was observed with naked eyes when a top-down observation was carried out by a top-down SEM. Evaluation results of the resist compositions of the present invention and the resist composition for comparison in the EUV drawing are shown in Table 8.

TABLE 8

| | Optimum Exposure Dose (mJ/cm²) | Limiting Resolution (nm) | LER (nm) | Pattern Profile |
|---|---|---|---|---|
| Example 35 | 15 | 28 | 4.0 | Rectangular |
| Example 36 | 14 | 30 | 4.3 | Rectangular |
| Example 37 | 14 | 28 | 4.2 | Rectangular |
| Example 38 | 14 | 28 | 4.2 | Rectangular |
| Comparative Example 9 | 12 | 50 | 9.6 | Rectangular |

The results in the above-mentioned Tables 7 and 8 are explained. The resist compositions (Examples 1 to 34 and 38, and Examples 35 to 38) containing the onium salt represented by the above-mentioned general formula (1) each showed good resolution and good pattern rectangularity, and also showed good values in line edge roughness. On the other hand, the resist compositions using the amine compound as the acid diffusion controlling agent or the resist compositions using the onium salt having no fluorine atom at the α-position of the carboxyl group of Comparative Examples 1 to 8 and Comparative Example 9 showed bad results in resolution, line edge roughness, PED and CDU as compared with those of Examples. When the amine compound was used, the acid generated from the sulfonic acid could not cause the exchange reaction with the amine compound, so that roughness was considered to become large. Also, the resist compositions using the onium salt having no fluorine atom at the α-position of the carboxyl group had a large difference in a pKa from that of the sulfonic acid, so that the cause of deterioration of roughness was considered to be a rapid exchange reaction which did not occur. In addition, when the onium salt having a pKa smaller than 1.5 was used in Comparative Examples 7 and 8, the resist was highly sensitive, and the value of the line edge roughness became large. This result can be considered that the pKa is high so that it did not act as the acid diffusion controlling agent but act as the acid generator.

As can be clearly seen from the explanation mentioned above, when the chemically amplified positive resist composition using the onium salt of the present invention is employed, a pattern with a little line edge roughness can be formed by exposure. The patterning process using the same is useful for photolithography in semiconductor manufacturing, in particular, in the processing of photomask blanks.

It must be stated here that the present invention is not restricted to the embodiments shown by the above-mentioned embodiments. The above-mentioned embodiments are merely examples so that any embodiments composed of substantially the same technical concept as disclosed in the claims of the present invention and expressing a similar effect are included in the technical scope of the present invention.

What is claimed is:

1. An onium salt represented by the following general formula (1) or (2),

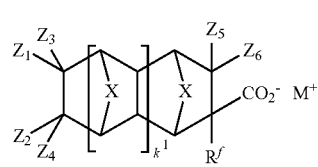

(1)

wherein $R^f$ represents a fluorine atom or a trifluoromethyl group; $M^+$ represents a monovalent cation; X represents O or $CH_2$; $k^1$ represents an integer of 0 to 2; and $Z^1$, $Z^2$, $Z^3$, $Z^4$, $Z^5$ and $Z^6$ each independently represent a hydrogen atom or a linear, branched or cyclic monovalent hydrocarbon group having 1 to 10 carbon atoms which may be substituted by a hetero atom(s), and a hetero atom(s) may be interposed in the monovalent hydrocarbon group,

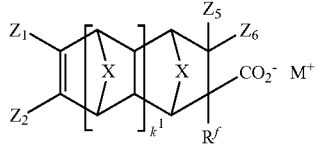

(2)

wherein $R^f$, X, $k^1$, $Z^1$, $Z^2$, $Z^5$, $Z^6$ and $M^+$ have the same meanings as defined above.

2. A chemically amplified positive resist composition which comprises the onium salt defined in claim 1, a resin having a group which can be decomposed by an acid, and a photoacid generator.

3. The chemically amplified positive resist composition according to claim 2, wherein the resin contains a repeating unit represented by the following general formula (3),

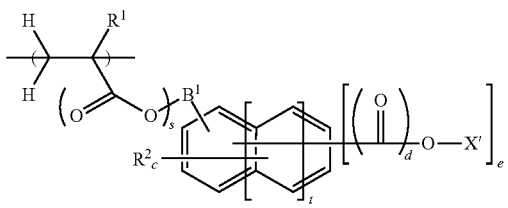

(3)

wherein "s" represents 0 or 1; "t" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "c" represents an integer satisfying $c \leq 5+2t-e$; "d" represents 0 or 1; "e" represents an integer of 1 to 3; and X' represents an acid-labile group when "e" represents 1, and represents a hydrogen atom or an acid-labile group when "e" represents 2 or more, and at least one of which represent an acid-labile group.

4. The chemically amplified positive resist composition according to claim 2, wherein the resin contains a repeating unit represented by the following general formula (4),

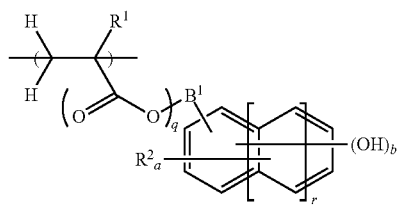

(4)

wherein "q" represents 0 or 1; "r" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "a" represents an integer satisfying $a \leq 5+2r-b$; and "b" represents an integer of 1 to 3.

5. The chemically amplified positive resist composition according to claim 3, wherein the resin contains a repeating unit represented by the following general formula (4),

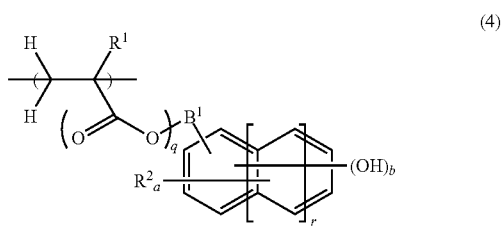

(4)

wherein "q" represents 0 or 1; "r" represents an integer of 0 to 2; $R^1$ represents a hydrogen atom, a fluorine atom, a methyl group or a trifluoromethyl group; each $R^2$ independently represents a hydrogen atom or an alkyl group having 1 to 6 carbon atoms; $B^1$ represents a single bond or an alkylene group having 1 to 10 carbon atoms which may contain an ether bond(s); "a" represents an integer satisfying $a \leq 5+2r-b$; and "b" represents an integer of 1 to 3.

6. The chemically amplified positive resist composition according to claim 2, wherein the resin contains a repeating unit represented by the following general formula (5) or a repeating unit represented by the following general formula (6), or both of them,

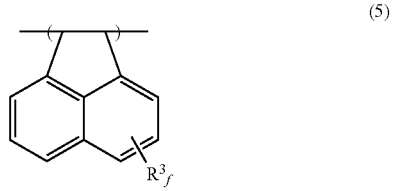

(5)

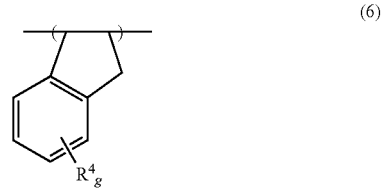

(6)

wherein "f" represents an integer of 0 to 6; each $R^3$ independently represents a hydrogen atom, an alkyl group having 1 to 6 carbon atoms which may be substituted by a halogen atom(s), a primary or secondary alkoxy group which may be substituted by a halogen atom(s), or an alkylcarbonyloxy group having 1 to 7 carbon atoms which may be substituted by a halogen atom(s); "g" represents an integer of 0 to 4; each $R^4$ independently represents a hydrogen atom, an alkyl group having 1 to 6 carbon atoms which may be substituted by a halogen atom(s), a primary or secondary alkoxy group which may be substituted by a halogen atom(s), or an alkylcarbonyloxy group having 1 to 7 carbon atoms which may be substituted by a halogen atom(s).

7. The chemically amplified positive resist composition according to claim 2, wherein the composition further comprises a basic compound.

* * * * *